(12) United States Patent
Kusuda

(10) Patent No.: US 7,230,709 B2
(45) Date of Patent: Jun. 12, 2007

(54) MEASURING METHOD AND MEASURING APPARATUS OF OPTICAL ENERGY ABSORPTION RATIO, AND THERMAL PROCESSING APPARATUS

(75) Inventor: Tatsufumi Kusuda, Kyoto (JP)

(73) Assignee: Dainippon Screen Mfg. Co., Ltd. (JP)

( * ) Notice: Subject to any disclaimer, the term of this patent is extended or adjusted under 35 U.S.C. 154(b) by 380 days.

(21) Appl. No.: 10/881,234

(22) Filed: Jun. 30, 2004

(65) Prior Publication Data

US 2005/0018196 A1    Jan. 27, 2005

(30) Foreign Application Priority Data

Jun. 30, 2003 (JP) ............................. 2003-187244
May 17, 2004 (JP) ............................. 2004-146634

(51) Int. Cl.
*G01N 21/00* (2006.01)

(52) U.S. Cl. ...................................... 356/432; 219/405

(58) Field of Classification Search ................ 219/390, 219/405, 411, 209, 220, 251, 258, 264, 399, 219/441, 446.1; 356/432, 448
See application file for complete search history.

(56) References Cited

U.S. PATENT DOCUMENTS

| | | | | |
|---|---|---|---|---|
| 4,336,279 A | * | 6/1982 | Metzger | 427/521 |
| 4,525,380 A | * | 6/1985 | Arai et al. | 438/787 |
| 4,649,261 A | | 3/1987 | Sheets | |
| 6,376,806 B2 | * | 4/2002 | Yoo | 219/411 |

FOREIGN PATENT DOCUMENTS

| | | |
|---|---|---|
| JP | 57-162340 | 10/1982 |
| JP | 59-169125 | 9/1984 |
| JP | 60-258928 | 12/1985 |
| JP | 63-166219 | 7/1988 |
| JP | 11-340157 | 12/1999 |

\* cited by examiner

*Primary Examiner*—Hoa Pham
*Assistant Examiner*—Tri Ton
(74) *Attorney, Agent, or Firm*—Ostrolenk, Faber, Gerb & Soffen, LLP

(57) ABSTRACT

Reflection intensities of a standard wafer with a known reflectance, a plain wafer on which no pattern is formed, and a semiconductor wafer to be processed practically are measured by using an optical measuring system. Their respective reflection intensities are subjected to spectral resolution processing. The optical energy value absorbed by the plain wafer is calculated from the reflection intensity of the standard wafer and the reflection intensity of the plain wafer. The absorbed optical energy value for the wafer is calculated from the reflection intensity of the standard wafer and the reflection intensity of the processing object wafer. Based on these, the optical energy absorption ratio of the processing object wafer to the plain wafer is calculated. From this optical energy absorption ratio and the optimum energy value of light irradiated to the plain wafer, the optimum energy value to be irradiated to the processing object wafer is calculated.

2 Claims, 13 Drawing Sheets

F I G . 5
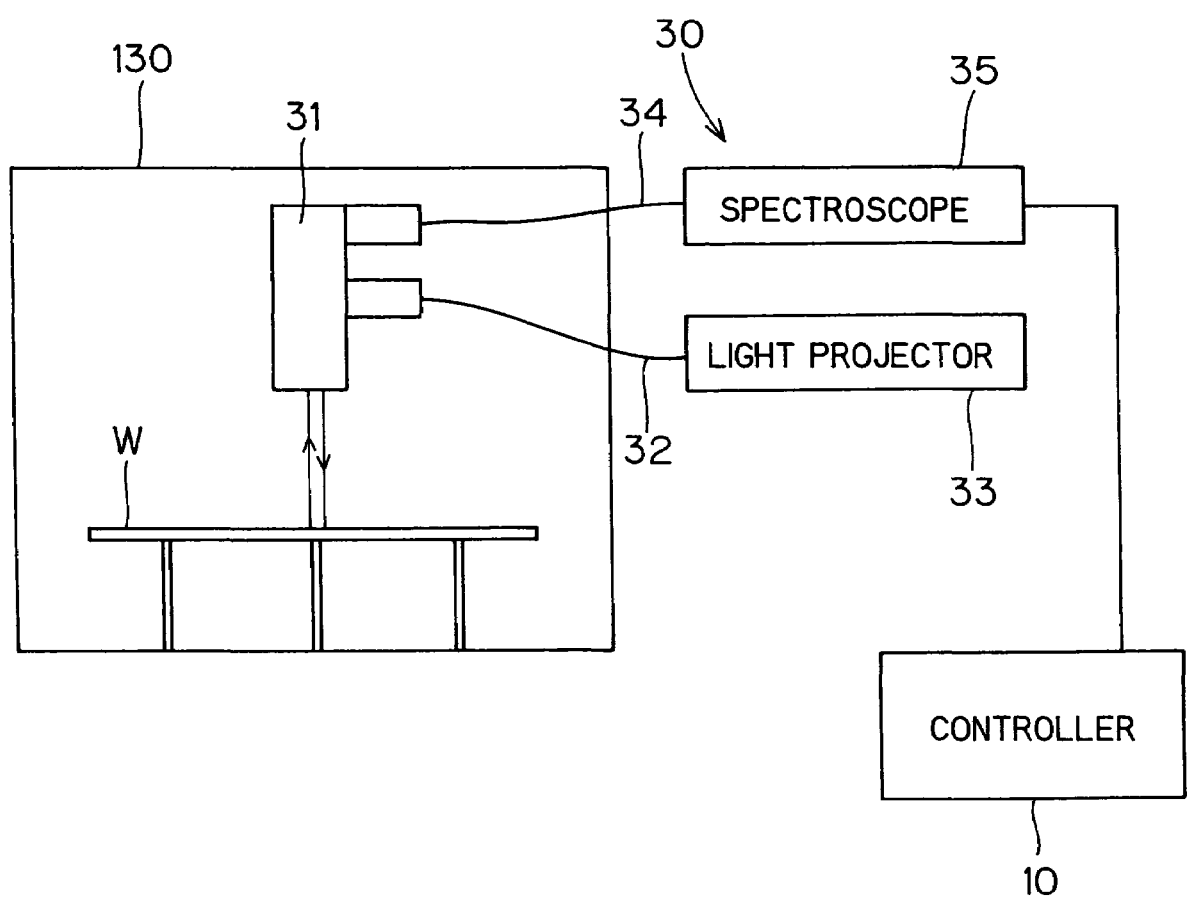

F I G . 6
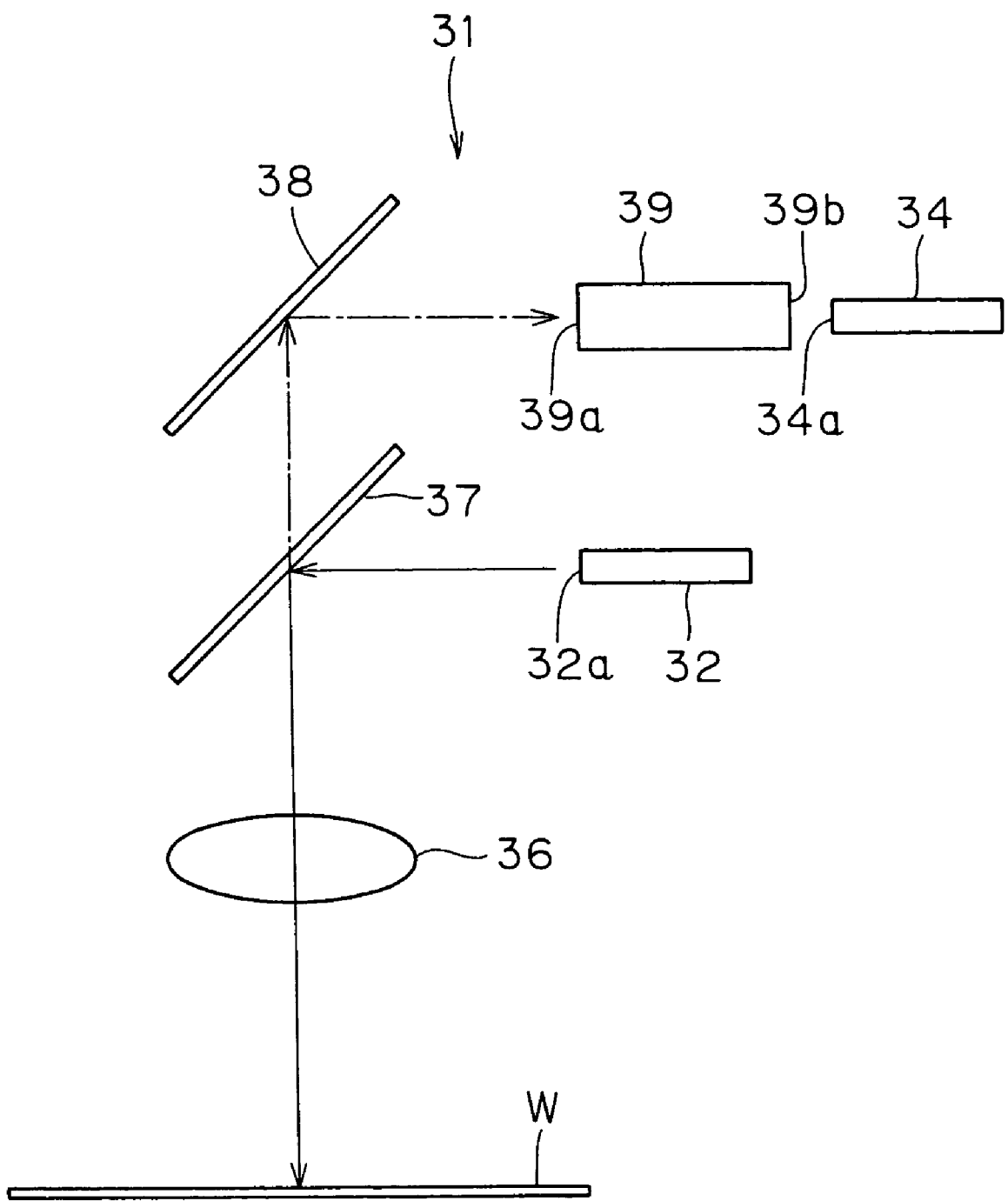

F I G . 1 1
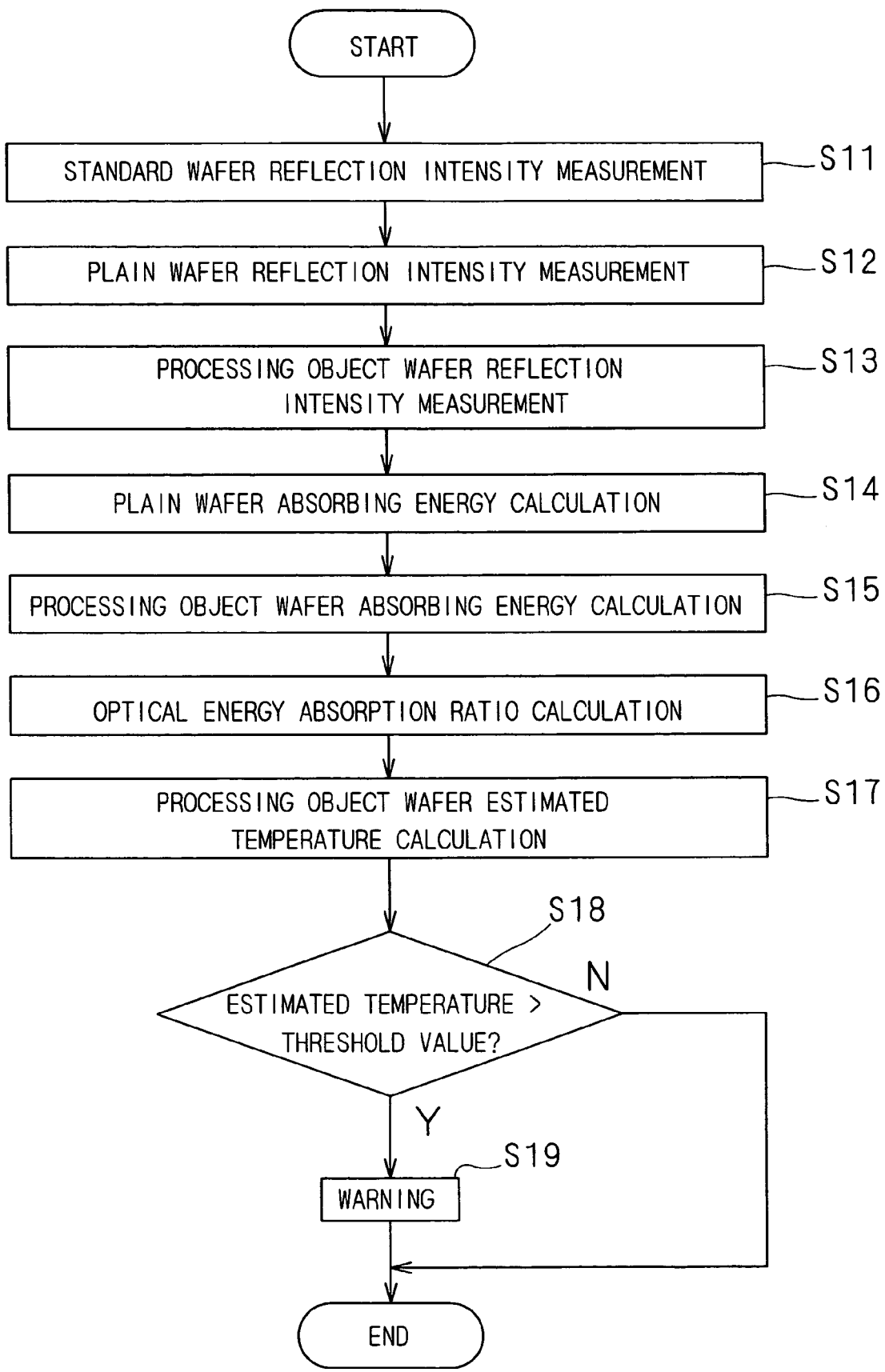

F I G . 1 2
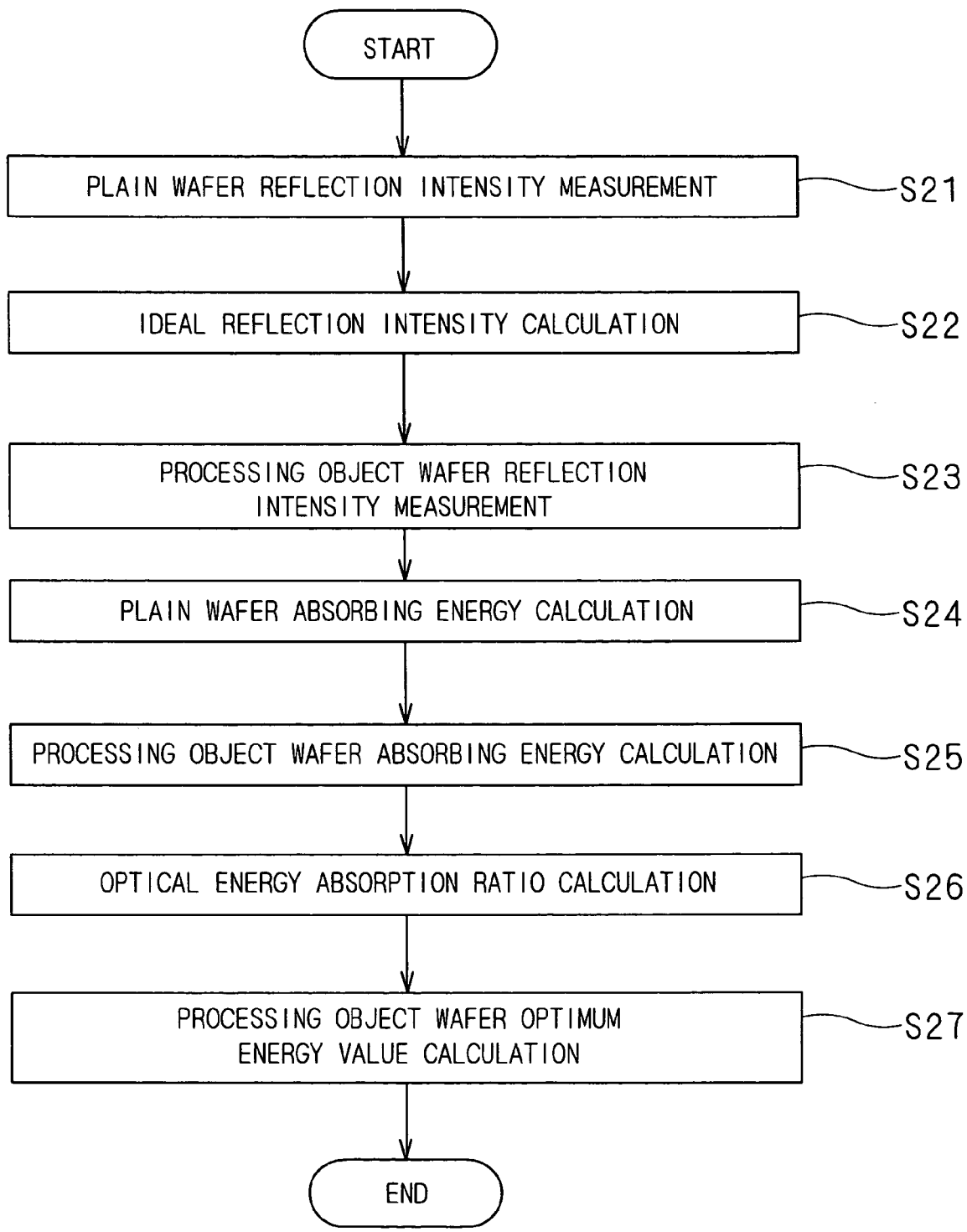

MEASURING METHOD AND MEASURING APPARATUS OF OPTICAL ENERGY ABSORPTION RATIO, AND THERMAL PROCESSING APPARATUS

BACKGROUND OF THE INVENTION

1. Field of the Invention

The present invention relates to a measuring method and a measuring apparatus for measuring optical energy absorption ratio of a processing object substrate to a plain substrate on which no pattern is formed, as well as a thermal processing apparatus employing such a measuring technique.

2. Description of the Background Art

In an ion activation step of a semiconductor wafer after being subjected to ion implantation, there has heretofore been used a thermal processing apparatus such as a lamp annealing apparatus using halogen lamps. In such a thermal processing apparatus, the ion activation of a semiconductor wafer is carried out by heating (annealing) the semiconductor wafer to temperatures of, for example, approximately 1000° C. to 1100° C. This thermal processing apparatus is constructed so as to elevate the temperature of the substrate at a speed of about several hundreds of degrees per second, by utilizing the energy of light irradiated from the halogen lamps.

However, even when the ion activation of a semiconductor wafer is executed with a thermal processing apparatus that elevates the temperature of the semiconductor wafer by halogen lamps at a speed of about several hundreds of degrees per second, the profile of ions implanted into the semiconductor wafer becomes round. That is, it has been found to cause the phenomenon that ions diffuse by heat. In case that this phenomenon occurs, even if ions are implanted at a high concentration into the semiconductor wafer surface, the implanted ions may diffuse. This introduces the problem that it is necessary to implant more ions than necessary.

In order to solve the above problem of ion diffusion, for example, Japanese Patent Application Laid-Open Nos. 59-169125 and 63-166219 have proposed such a technique that only the temperature of the surface of a semiconductor wafer after being subjected to ion implantation is elevated in an extremely short period of time (not exceeding several milliseconds) by irradiating flashlight to the surface of the semiconductor wafer by use of xenon flash lamps, etc. For the temperature elevation in a very short time by the xenon flash lamps, the ions will not have a sufficient time to diffuse. Therefore only the ion activation is executable without rounding the profile of ions implanted into the wafer.

However, in a thermal processing apparatus using xenon flash lamps, very enormous optical energy is irradiated to the wafer surface in an extremely short period of time. This causes a rapid elevation of the surface temperature thereof, so that only the wafer surface expands rapidly. It has been found that any excess energy irradiated from the xenon flash lamps causes only the wafer surface to expand rapidly, thus leading to a slip in the wafer surface, and the wafer break in the very worst case. On the other hand, it is impossible to carry out ion activation if irradiation energy is insufficient. It is therefore important to optimize the range of optical energy irradiated from the xenon flash lamps.

In general, with flash lamps of which irradiation time is extremely short, it is impossible to perform feedback control of lamp output on the basis of the measuring result of the temperature of a semiconductor wafer. Hence, there is first performed ion implantation of a plain bare wafer on which no pattern is formed, and the plain wafer after being subjected to the ion implantation is then subjected to actual light irradiation. Thereafter, the characteristics after processing (e.g., sheet resistance value) is measured, and the optical energy irradiated from the xenon flash lamps is adjusted on the basis of the measuring result.

However, a pattern is already formed on a wafer to be processed practically, and therefore it often has optical absorption characteristics different from that of a plain wafer. Usually, even if the light of the same energy is irradiated, a wafer on which a pattern is formed tends to absorb more optical energy than a plain wafer. Hence, even if the irradiation energy to the plain wafer is optimized, the wafer processed practically absorbs even more, which can create the problem of causing wafer break. To avoid this, optimum irradiation energy for plain wafer must be compensatory to each processing object wafer.

SUMMARY OF THE INVENTION

The present invention is directed to a measuring apparatus for measuring an optical energy absorption ratio of a processing object substrate to a plain substrate on which no pattern is formed.

The measuring apparatus includes: a plain substrate reflection intensity obtaining element for obtaining a plain substrate reflection intensity by measuring spectral characteristics of reflection intensity of a reflected light obtained when irradiating light to a plain substrate with a known reflectance; an ideal reflection intensity calculating element for calculating an ideal reflection intensity that is a spectral reflection intensity of a reflected light when irradiating light to an ideal mirror of which reflectance is 100%, on the basis of the plain substrate reflection intensity and the reflectance; a processing object substrate reflection intensity obtaining element for obtaining a processing object substrate reflection intensity by measuring spectral characteristics of reflection intensity of a reflected light obtained when irradiating light to the processing object substrate; a plain substrate absorbing energy calculating element for calculating optical energy absorbed by the plain substrate from the ideal reflection intensity and the plain substrate reflection intensity; a processing object substrate absorbing energy calculating element for calculating optical energy absorbed by the processing object substrate from the ideal reflection intensity and the processing object substrate reflection intensity; and an absorption ratio calculating element for calculating an optical energy absorption ratio of the processing object substrate to the plain substrate from the optical energy absorbed by the plain substrate and the optical energy absorbed by the processing object substrate.

It is capable of simply measuring the optical energy absorption ratio of the processing object substrate to the plain substrate.

The present invention is also directed to a thermal processing apparatus for heating a processing object substrate by irradiating light to the substrate, with a known optimum energy value of light irradiated to a plain substrate on which no pattern is formed.

The thermal processing apparatus includes: a) holing means for holding a processing object substrate; b) irradiation means with a lamp for irradiating light to the processing object substrate held by the holding means; c) a measuring apparatus including: c-1) plain substrate reflection intensity obtaining means for obtaining a plain substrate reflection intensity by measuring spectral characteristics of reflection intensity of a reflected light obtained when irradiating light to a plain substrate with a known reflectance; c-2) ideal reflection intensity calculating means for calculating an ideal reflection intensity that is a spectral reflection intensity of a reflected light when irradiating light to an ideal mirror of which reflectance is 100%, on the basis of the plain substrate reflection intensity and the reflectance; c-3) processing object substrate reflection intensity obtaining means for obtaining a processing object substrate reflection intensity by measuring spectral characteristics of reflection intensity of a reflected light obtained when irradiating light to the processing object substrate; c-4) plain substrate absorbing energy calculating means for calculating optical energy absorbed by the plain substrate from the ideal reflection intensity and the plain substrate reflection intensity; c-5) processing object substrate absorbing energy calculating means for calculating optical energy absorbed by the processing object substrate from the ideal reflection intensity and the processing object substrate reflection intensity; and c-6) absorption ratio calculating means for calculating an optical energy absorption ratio of the processing object substrate to the plain substrate from the optical energy absorbed by the plain substrate and the optical energy absorbed by the processing object substrate; and d) optical energy control means for adjusting the energy of light irradiated from the irradiation means to the processing object substrate, on the basis of the optical energy absorption ratio obtained by the measuring apparatus and the optimum energy value of light irradiated to the plain substrate.

It is capable of preventing damage to the processing object substrate during thermal processing.

The present invention is also directed to a measuring method for measuring an optical energy absorption ratio of a processing object substrate to a plain substrate on which no pattern is formed.

Accordingly, it is an object of the present invention to provide a measuring technique with which it is able to simply measure the optical energy absorption ratio of a processing object substrate to a plain substrate on which no pattern is formed.

It is other object of the present invention to provide a thermal processing apparatus capable of preventing damage to a processing object substrate during thermal processing.

These and other objects, features, aspects and advantages of the present invention will become more apparent from the following detailed description of the present invention when taken in conjunction with the accompanying drawings.

BRIEF DESCRIPTION OF THE DRAWINGS

FIG. 5 is a diagram showing the construction of an absorption ratio measuring apparatus disposed in an alignment part;

FIG. 6 is a diagram to explain the construction of a measuring optical system;

FIG. 11 is a flowchart showing a procedure in calculating an estimated temperature when heating an object semiconductor wafer;

FIG. 12 is a flowchart showing other example of the procedure in measuring an optical energy absorption ratio of a semiconductor wafer.

DESCRIPTION OF THE PREFERRED EMBODIMENTS

Preferred embodiments of the present invention are now described in detail by referring to the accompanying drawings.

1. First Preferred Embodiment

Figure 1:
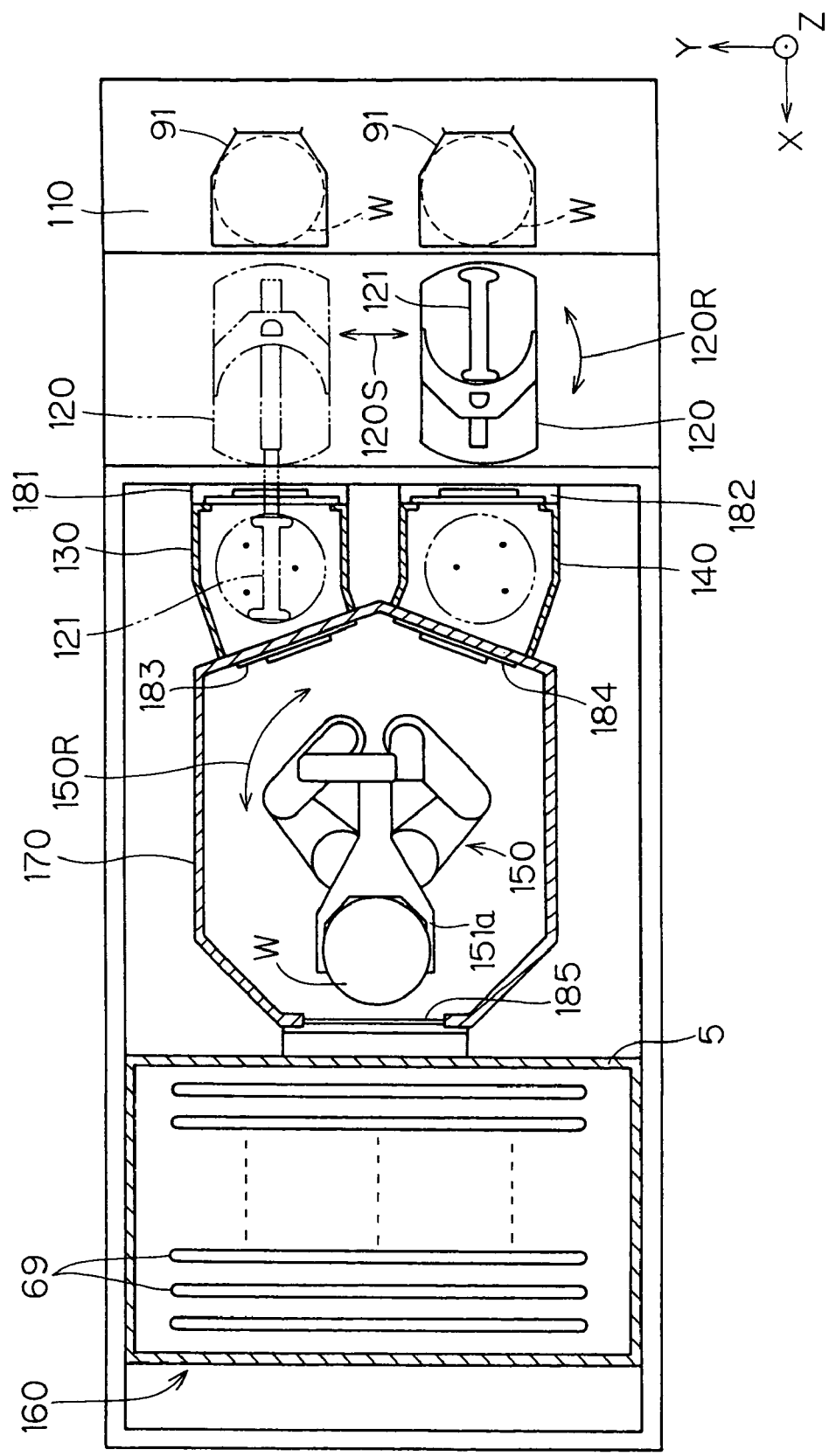
FIG. 1 is a plan view showing a thermal processing apparatus according to the present invention.
Figure 2:
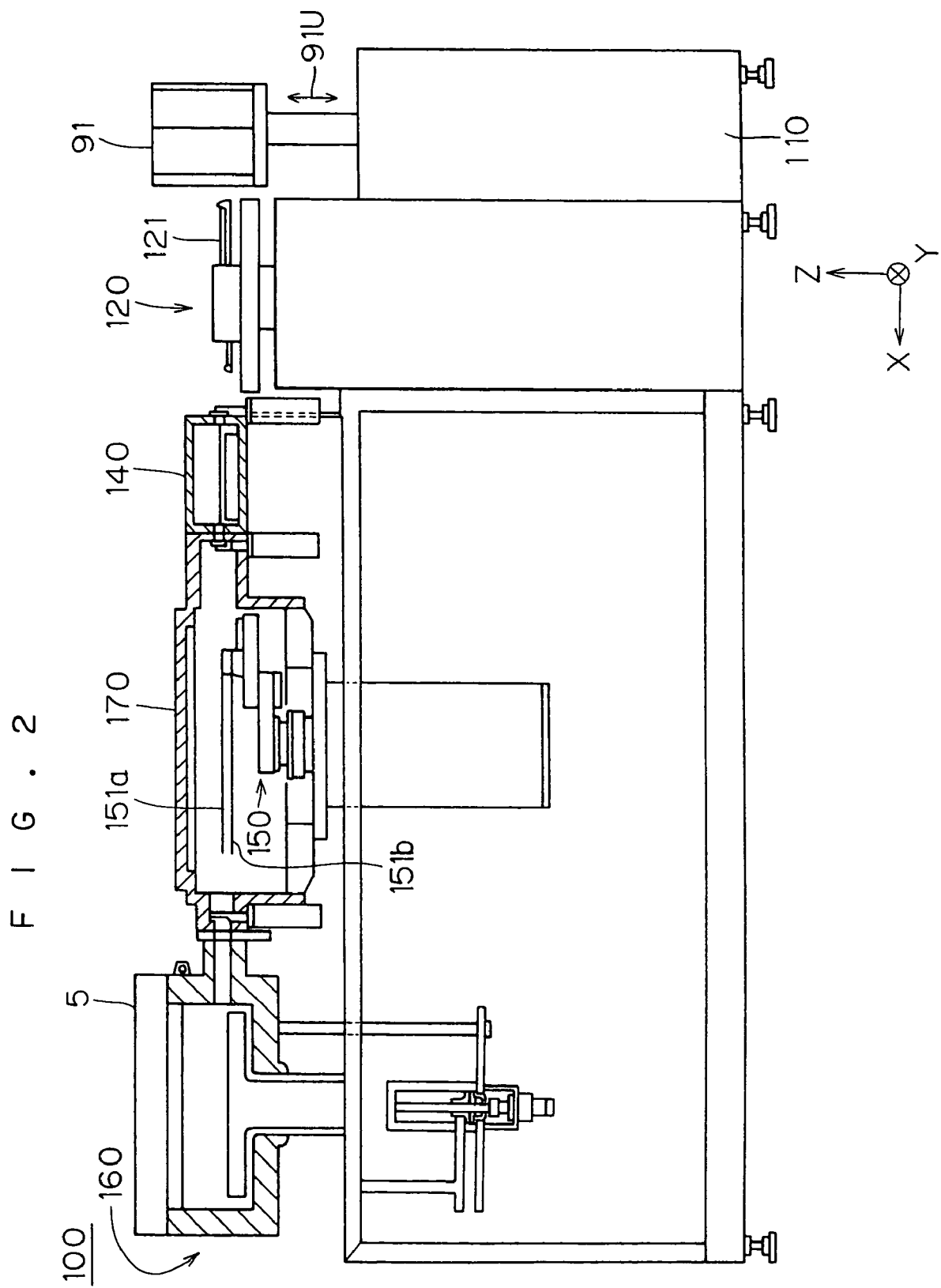
FIG. 2 is a front view showing the thermal processing apparatus of the present invention.

FIG. 1 and FIG. 2 are a plan view and a front view of a thermal processing apparatus 100 according to the present invention, respectively. For purposes of convenience, FIGS. 1 and 2 are partially sectioned, and the details are shown in simplified form. In order to clarify the directional relationship in FIGS. 1, 2, and the rest, where necessary, an XYZ rectangular coordinate system is appended, wherein the Z-axis direction is a vertical direction and an XY plane is a horizontal plane.

Referring to FIGS. 1 and 2, the thermal processing apparatus 100 has a substrate storing part (indexer) 110, on which two carriers 91 are mounted; a transfer robot 120 for loading and unloading a semiconductor wafer W with respect to the substrate storing part 110; an alignment part (aligner) 130 for aligning an untreated semiconductor wafer W; a cooling part (cooler) 140 for cooling a treated semiconductor wafer W; a transfer robot 150 for loading and unloading a semiconductor wafer W with respect to the alignment part 130, the cooling part 140 and the like; and a processing part 160 for subjecting a semiconductor wafer W to flash heat treatment.

There is further provided a transport room 170 for housing the transport robot 150 as a transport space of a semiconductor wafer W by the transport robot 150. The alignment part 130, the cooling part 140 and the processing part 160 are connected to the transport room 170.

The substrate storing part 110 is a section to which the carrier 91 is transported by an automatic guided vehicle (AGV) or the like and then mounted thereon. A semiconductor wafer W is, in the state of being stored in the carrier 91, loaded to and unloaded from the thermal processing apparatus 100. In the substrate storing part 110, the carrier 91 is constructed to move up and down as indicated by an arrow 91U such that the transfer robot 120 is capable of transferring any semiconductor wafer W.

The transfer robot 120 is capable of moving slidingly as indicated by a double-headed arrow 120S, and also capable of rotating as indicated by a double-headed arrow 120R. Thereby, the transfer robot 120 transfers a semiconductor wafer W to the two carriers 91, and also transfers the semiconductor wafer W to the alignment part 130 and the cooling part 140.

The transfer of the semiconductor wafers W to the carriers 91 by means of the transfer robot 120 are attained by slidingly moving a hand 121 and the up and down movement of the carriers 91. The transfer of the semiconductor wafer W between the transfer robot 120 and the alignment part 130 or the cooling part 140 is executed by sliding movement of the hand 121 and by the ascent and descent of the semiconductor wafers W with use of pins (i.e., the pins pushing up the semiconductor wafer W in the alignment part 130 and the cooling part 140).

The transfer robot 120 transfers a semiconductor wafer W to the alignment part 130 such that the center of the semiconductor wafer W is located at a predetermined position. The alignment part 130 rotates the semiconductor wafer W so as to face a proper direction. The alignment part 130 also has an absorption ratio measuring apparatus to be described later, which is used to measure the optical energy absorption ratio of the semiconductor wafer W to be subjected to thermal processing.

The transport robot 150 is capable of turning around an axis extending vertically as indicated by a double-headed arrow 150R. The transport robot 150 has two link mechanisms each composed of a plurality of arm segments. Transport arms 151a and 151b for holding a semiconductor wafer W are provided at the ends of the two link mechanisms, respectively. The transport arms 151a and 151b are vertically disposed a predetermined pitch apart, each of which is independently slidable linearly in the same horizontal direction. The transport robot 150 imparts up and down movement to a base on which the two link mechanisms are disposed, so that the two transport arms 151a and 151b move up and down with the predetermined pitch apart.

When the transport robot 150 performs transfer (loading/unloading) of a semiconductor wafer W with a transfer partner that is the alignment part 130, the processing part 160 or the cooling part 140, firstly, the transport arms 151a and 151b turn so as to oppose to the transfer partner, and then (or during the turn) moves up and down so that either of the transport arms is located at a height at which it performs transfer with the transfer partner. Thereafter, the transport arm 151a (151b) is slidingly moved linearly in a horizontal direction, thereby performing transfer of a semiconductor wafer W.

The processing part 160 is a section of performing heat treatment by irradiating the flashes from xenon flash lamps 69 (hereinafter also referred to simply as "flash lamps 69") to a semiconductor wafer W.

Since a semiconductor wafer W immediately after being subjected to the processing in the processing part 160 has a high temperature, the semiconductor wafer W is transferred to the cooling part 140 by the transport robot 150, followed by cooling. The semiconductor wafer W cooled in the cooling part 140 is then returned as a treated semiconductor wafer W to the carrier 91 by the transfer robot 120.

As described previously, in the thermal processing apparatus 100, the transport room 170 surrounds the periphery of the transport robot 150. The alignment part 130, the cooling part 140 and the processing part 160 are connected to the transport room 170. Gate valves 181 and 182 are provided between the transfer robot 120 and the alignment part 130 or the cooling part 140, respectively. Gate valves 183, 184 and 185 are provided between the transport room 170 and the alignment part 130 or the cooling part 140 or the processing part 160, respectively. From a nitrogen gas supply part (not shown), high purity nitrogen gas is supplied to the insides of the alignment part 130, the cooling part 140 and the transport room 170 such that they are kept clean, and an excess nitrogen gas is exhausted suitably through an exhaust pipe. These gate valves are suitably opened and closed when a semiconductor wafer W is transferred.

The alignment part 130 and the cooling part 140 are located at different positions between the transfer robot 120 and the transport robot 150. A semiconductor wafer W is temporarily mounted for alignment in the alignment part 130. A treated semiconductor wafer W is temporarily mounted for cooling in the cooling part 140.

Figure 3:
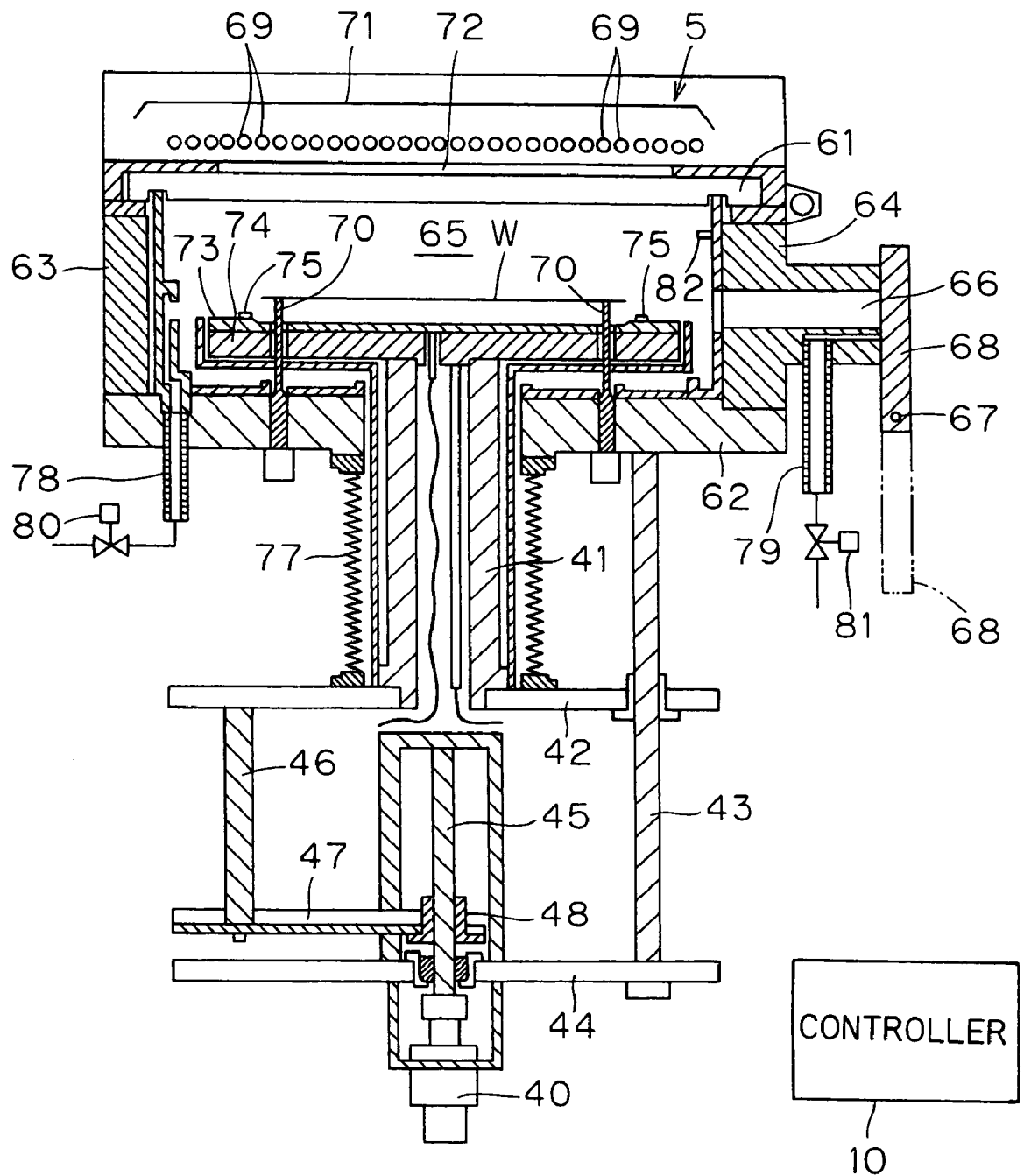
FIGS. 3 and 4 are side sectional views showing a processing part of the thermal processing apparatus of FIG. 1.
Figure 4:
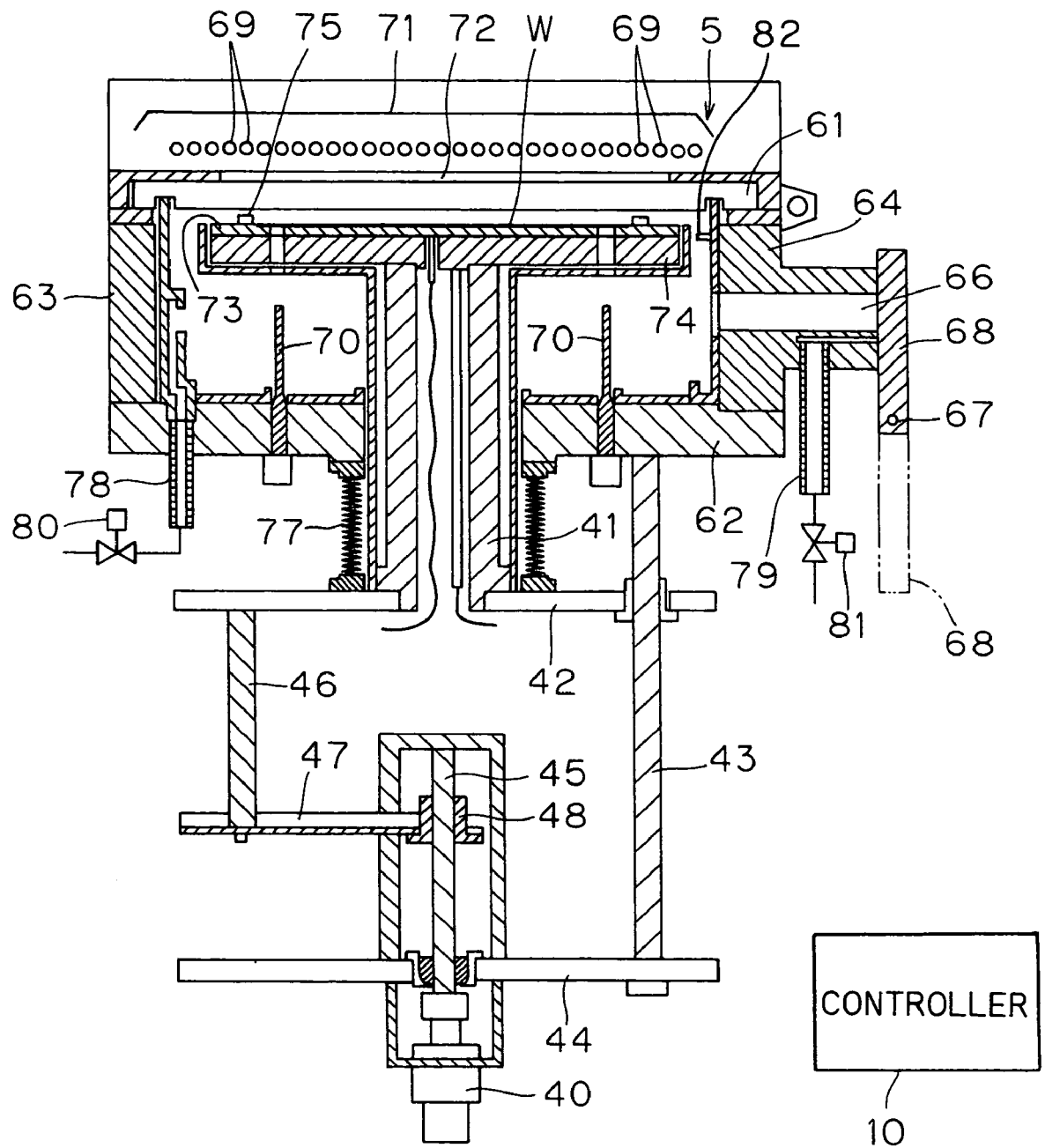

Next, the construction of the processing part 160 will be further described. FIGS. 3 and 4 are side sectional views showing the processing part 160 of the thermal processing apparatus 100 according to the present invention. Flash heating of substrates such as semiconductor wafers and the like is performed in the processing part 160.

The processing part 160 has a chamber 65. The chamber 65 consists of a translucent plate 61, a bottom plate 62, and a pair of side plates 63, 64, and performs thermal processing with a semiconductor wafer W stored in the inside thereof. The translucent plate 61 forming an upper part of the chamber 65 is composed of an infrared-transparent material such as quarts. The translucent plate 61 functions as a chamber window through which the light emitted from the flash lamps 69 is transmitted and introduced into the chamber 65. Support pins 70 are disposed vertically on the bottom plate 62 forming the chamber 65. The support pins 70 pass through holding means consisting of a susceptor 73 and a heating plate 74, each being described later, and support a semiconductor wafer W from the lower surface thereof.

An opening part 66, through which a semiconductor wafer W is loaded and unloaded, is formed in the side plate 64 forming the chamber 65. The opening part 66 can be opened and closed by the gate valve 68 rotating around the axis 67. The semiconductor wafer W is loaded, with the opening part 66 opened, into the chamber 65 by the transport robot 150. The gate valve 68 closes the opening part 66 when the semiconductor wafer W is subjected to thermal processing in the chamber 65.

The chamber 65 is disposed under the light source 5. The light source 5 contains a plurality of flash lamps 69 (thirty pieces in this preferred embodiment) and a reflector 71. The plurality of flash lamps 69 are bar-like lamps each having an elongated cylindrical shape and are arranged in parallel to one another such that their respective longitudinal directions extend in a horizontal direction. The reflector 71 is disposed above the flash lamps 69 so as to cover all of them.

Each xenon flash lamp 69 has a glass tube filled with xenon gas, both ends of which are respectively provided with an anode and a cathode that are connected to a capacitor, and a trigger electrode that is wound around the peripheral part of the glass tube. Xenon gas is electrically insulator and no current flows in the glass tube in the normal state. However, when a high voltage is applied to the trigger electrode in order to break insulation, the current stored in the capacitor flows momentarily in the glass tube, and Joule heat generated at that time heats the xenon gas to emit light. In the xenon flash lamp 69, electrostatic energy previously stored is converted to extremely short optical pulses of 0.1 milliseconds to 10 milliseconds. Therefore, the flash lamp 69 has the characteristic of being able to irradiate extremely more intense light than a lamp source of continuous lighting.

A light diffuser 72 is disposed between the light source 5 and the translucent plate 61. The light diffuser 72 is formed by performing light diffusion processing of the surface of a quartz glass as a light transmitting material. Alternatively, instead of the use of the light diffuser 72, the translucent plate 61 may be subjected to surface finish.

Part of the light emitted from each flash lamp 69 passes directly through the light diffuser 72 and the translucent plate 61 into the chamber 65. Other part of the light emitted from the flash lamp 69 is first reflected by the reflector 71 and then passes through the light diffuser 72 and the translucent plate 61 into the chamber 65.

The heating plate 74 and the susceptor 73 are disposed in the chamber 65. The susceptor 73 is stuck on an upper surface of the heating plate 74. Pins 75 for preventing dislocation of a semiconductor wafer W are provided on the surface of the susceptor 73.

The heating plate 74 is used for preheating (i.e., assist heating) a semiconductor wafer W. The heating plate 74 is made of aluminum nitride and has in its inside a heater and a sensor for controlling the heater. On the other hand, the susceptor 73 is used to preheat uniformly a semiconductor wafer W by diffusing thermal energy from the heating plate 74. As a material of the susceptor 73, quartz, high purity ceramics, and the like can be used. Alternatively, like the heating plate 74, the susceptor 73 may also be composed of aluminum nitride.

Arrangement is such that a motor 40 drives the susceptor 73 and the heating plate 74 to move up and down between the loading and unloading positions of a semiconductor wafer W, as shown in FIG. 3, and the thermal processing position of the semiconductor wafer W, as shown in FIG. 4.

Specifically, the heating plate 74 is connected via a cylindrical body 41 to a moving plate 42. A guide member 43 suspended from the bottom plate 62 of the chamber 65 guides the moving plate 42 in up and down movement. A stationary plate 44 is fixed to a lower end part of the guide member 43, and the motor 40 that drives a ball screw 45 to rotate is disposed at a central part of the stationary plate 44. The ball screw 45 is screwed on a nut 48 connected via connecting members 46 and 47 to the moving plate 42. Thus, by the driving of the motor 40, the susceptor 73 and the heating plate 74 can move up and down between the loading and unloading positions shown in FIG. 3, and the thermal processing position shown in FIG. 4.

The loading and unloading positions of a semiconductor wafer W shown in FIG. 3 correspond to a position obtained when the susceptor 73 and the heating plate 74 are lowered in order that a semiconductor wafer W to be loaded through the opening part 66 by the transport robot 150 is mounted on the support pins 70, alternatively, that the semiconductor wafer W mounted on the support pins 70 is unloaded through the opening part 66. In this state, the upper end of the support pins 70 passes through each through hole formed in the susceptor 73 and the heating plate 74, and then projects beyond the surface of the susceptor 73.

On the other hand, the thermal processing position of a semiconductor wafer W shown in FIG. 4 corresponds to a position obtained when the susceptor 73 and the heating plate 74 are raised above the upper end of the support pins 70 in order to perform thermal processing of the semiconductor wafer W. In the process that the susceptor 73 and the heating plate 74 move up from the loading and unloading positions in FIG. 3 to the thermal processing position in FIG. 4, the semiconductor wafer W mounted on the support pins 70 is received by the susceptor 73, and raised with its lower surface supported by the surface of the susceptor 73, and then held in a horizontal position at a location close to the translucent plate 61 in the chamber 65. In contrast, in the process that the susceptor 73 and the heating plate 74 move down from the thermal processing position to the loading and unloading positions, the semiconductor wafer W supported by the susceptor 73 is transferred to the support pins 70.

When the susceptor 73 and the heating plate 74 that hold the semiconductor wafer W are raised to the thermal processing position, the translucent plate 61 is located between the semiconductor wafer W held by them and the light source 5. Note that the distance between the susceptor 73 and the light source 5 at that time is adjustable to any value by controlling the amount of rotation of the motor 40.

Between the bottom plate 62 of the chamber 65 and the moving plate 42, there is disposed an extensible bellows 77 that surrounds the periphery of the cylindrical body 41 so as to maintain the chamber 65 in an airtight state. The bellows 77 shrinks when the susceptor 73 and the heating plate 74 have been raised to the thermal processing position, and it extends when they have been lowered to the loading and unloading positions, thereby separating the atmosphere of the chamber 65 from the external atmosphere.

An introduction path 78 connected in communication to a switching valve 80 is formed in a side plate 63 that is disposed the opposite side of the opening part 66 in the chamber 65. Through the introduction path 78, gas required for processing such as inactive nitrogen gas is introduced into the chamber 65. A discharge path 79 connected in communication to a switching valve 81 is formed in the opening part 66 of the side plate 64. The discharge path 79 is used to exhaust the gas in the chamber 65 and connected via the switching valve 81 to exhaust means (not shown).

Further, an optical guide 82 is disposed on the inner wall of the side plate 64 in the chamber 65. As shown in FIG. 4, the optical guide 82 is arranged to locate in the vicinity of the heating plate 74 when the susceptor 73 and the heating plate 74 are raised to the thermal processing position. The optical guide 82 is composed of a quartz rod and an optical fiber, and receives the light irradiated from the flash lamps 69, and leads it out to a power monitor 83 in the outside of the chamber 65 (see FIG. 7). The power monitor 83 receives the light lead by the optical guide 82, and measures mainly the intensity of visible radiation region of the light irradiated from the flash lamps 69.

In the thermal processing apparatus 100 of this preferred embodiment, an absorption ratio measuring apparatus is disposed in the alignment part 130. FIG. 5 is a diagram showing the configuration of an absorption ratio measuring apparatus 30. The absorption ratio measuring apparatus 30 includes a measuring optical system 31, a light projector 33 connected via a light-projection optical fiber 32 to the measuring optical system 31, and a spectroscope 35 connected via a light-receiving optical fiber 34 to the measuring optical system 31. The light projector 33 generates light having a constant quantity of light. The light irradiated from the light projector 33 is irradiated from the measuring optical system 31 to the surface of a semiconductor wafer W held by the pins of the alignment part 130, and then reflected from the surface of the semiconductor wafer W. Arrangement is such that the reflected light is given, via the measuring optical system 31, from the light-receiving optical fiber 34 to the spectroscope 35. An output signal of the spectroscope 35 is inputted to a controller 10.

FIG. 6 is a diagram to explain the configuration of the measuring optical system 31. In the measuring optical system 31, an achromatic lens 36, a half mirror 37 and a total reflection mirror 38 are arrayed vertically in bottom-to-top order. A diffuser 39 is also disposed in the direction in which the reflected light from the total reflection mirror 38 travels.

The half mirror 37 is disposed at an angle of 45° to the semiconductor wafer W held by the pins of the alignment part 130 (i.e., an angle of 45° to a horizontal plane). The half mirror 37 receives a horizontal light from an emission end 32*a* of the light-projection optical fiber 32, and reflects it in a vertical downward direction toward the surface of the semiconductor wafer W. The light reflected from the half mirror 37 passes through the achromatic lens 36 to the surface of the surface of the semiconductor wafer W.

The reflected light reflected from the surface of the semiconductor wafer W passes through the achromatic lens 36 and then the half mirror 37, and is reflected from the total reflection mirror 38 toward the diffuser 39. The reflected light that enters the diffuser 39 is subjected to diffusion homogenization processing, and enters an incident end 34a of the light-receiving optical fiber 34.

In other words, the diffuser 39 is interposed between the incident end 34a of the light-receiving optical fiber 34 and the total reflection mirror 38. An incident end face 39a of the diffuser 39 is opposed to the total reflection mirror 38, and its emission end face 39b is opposed to the incident end 34a of the light-receiving optical fiber 34. The achromatic lens 36 also functions to converge the reflected light from the semiconductor wafer W onto the incident end face 39a of the diffuser 39.

The light that enters the light-receiving optical fiber 34 is subjected to spectral resolution processing by the spectroscope 35, and a signal that the spectroscope 35 outputs as the result of this processing is inputted to the controller 10. The controller 10 calculates the optical energy absorption ratio of the semiconductor wafer W in such a manner as described later.

Figure 7:
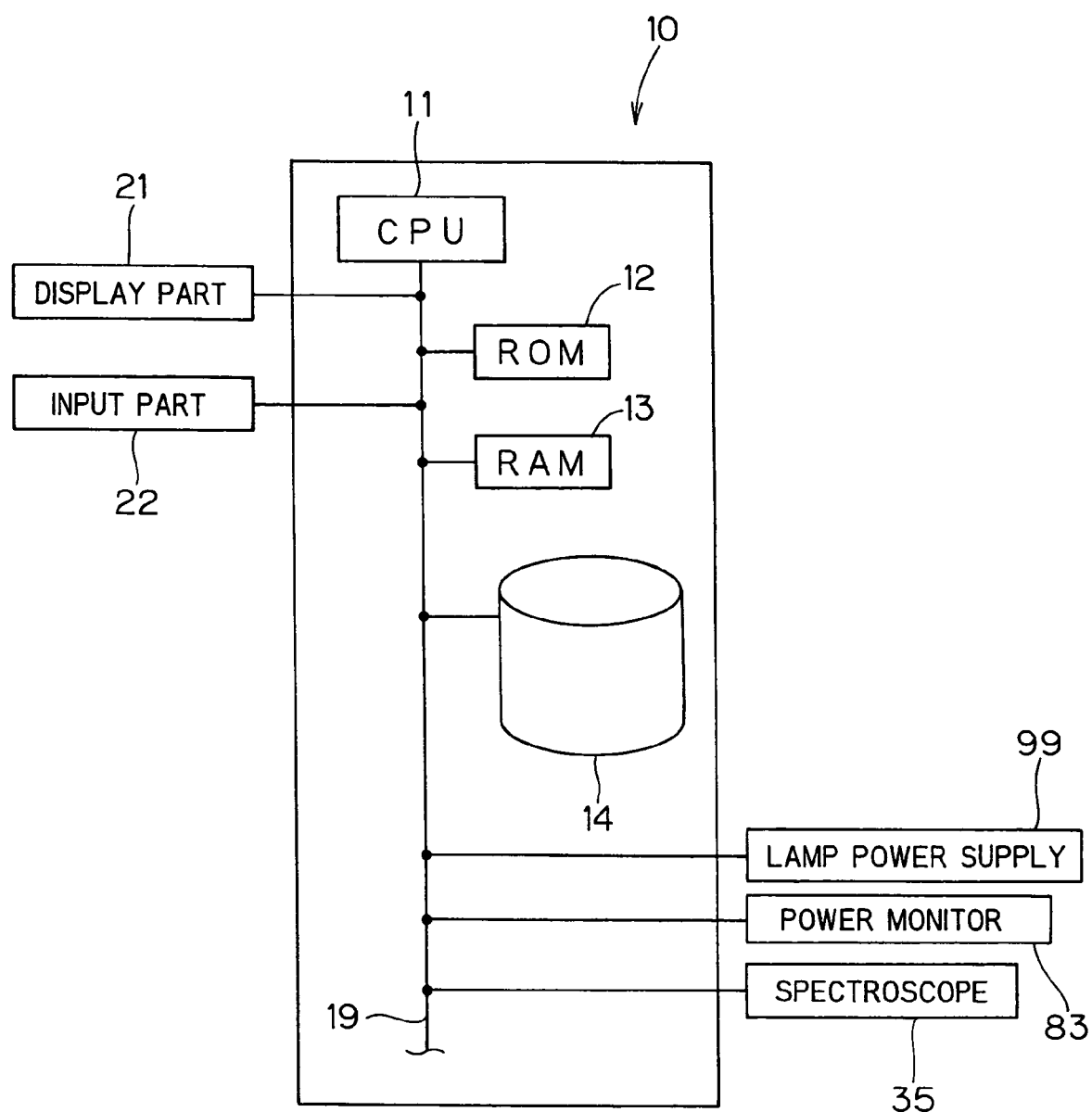
FIG. 7 is a block diagram showing the construction of a controller.

The controller 10 controls the processing part 160 and the absorption ratio measuring apparatus 30 in the thermal processing apparatus 100, and also calculates the optical energy absorption ratio of the semiconductor wafer W held by the alignment part 130 in such a manner as described later. FIG. 7 is a block diagram showing the configuration of the controller 10. The configuration of the controller 10 as hardware is similar to a general computer. Specifically, the controller 10 is configured by connecting, on a bus line 19, a CPU 11 performing various arithmetic processing, a ROM 12 that is a read only memory for storing a basic program, a RAM 13 that is a random access memory for storing various information, and a magnetic disk 14 for storing software for control and data.

A lamp power supply 99 of the processing part 160, the spectroscope 35 of the absorption ratio measuring apparatus 30, and the power monitor 83 are electrically connected to the bus line 19. The CPU 11 of the controller 10 executes the software for control stored in the magnetic disk 14 in order to measure the optical energy absorption ratio of a semiconductor wafer W to a plain wafer on which no pattern is formed, and to adjust power supplied to the flash lamps 69.

Further, a display part 21 and an input part 22 are electrically connected to the bus line 19. The display part 21 is constructed by using a crystal liquid display or the like, and displays a variety of information such as processing results and recipe contents. The input part 22 is constructed by using such as a keyboard and a mouse, and accepts inputs such as commands and parameters. An operator of the apparatus can input commands, parameters and the like through the input part 22, while confirming the content displayed on the display part 21. Alternatively, the display part 21 and the input part 22 may be integrated to configure as a touch panel.

The following is a thermal processing operation of a semiconductor wafer W in the thermal processing apparatus 100 according to the present invention. A semiconductor wafer W that is a processing object of the thermal processing apparatus 100 is a semiconductor wafer after being subjected to ion implantation. After a description of a wafer flow in the entire thermal processing apparatus 100, there will be described measurement of the optical energy absorption ratio of the semiconductor wafer W by the absorption ratio measuring apparatus 30, and the processing contents in the processing part 160.

In the thermal processing apparatus 100, first, a plurality of semiconductor wafers W after being subjected to ion implantation, which are in the state of being stored in the carrier 91, are mounted on the substrate storing part 110. Then the transfer robot 120 takes the semiconductor wafers W one by one from the carrier 91, and transfers them to the alignment part 130. In the alignment part 130, besides the alignment of the semiconductor wafers W, optical energy absorption ratio measurement is made by the absorption ratio measuring apparatus 30.

The semiconductor wafer W aligned in the alignment part 130 is taken into the transport room 170 by the transport arm 151a on the upper side of the transport robot 150, and the transport robot 150 turns to face the processing part 160.

At the moment that the transport robot 150 faces the processing part 160, the lower transport arm 151b takes the preceding treated semiconductor wafer W from the processing part 160, and the upper transport arm 151a loads an untreated semiconductor wafer W into the processing part 160. At this moment, the transport robot 150 slidingly moves the transport arms 151a and 151b in a direction perpendicular to the longitudinal direction of the flash lamps 69.

Subsequently, the transport robot 150 turns to face the cooling part 140, and the lower transport arm 151b transfers the treated semiconductor wafer W to the cooling part 140. The semiconductor wafer W cooled in the cooling part 140 is then returned to the carrier 91 by the transfer robot 120.

Figure 8:
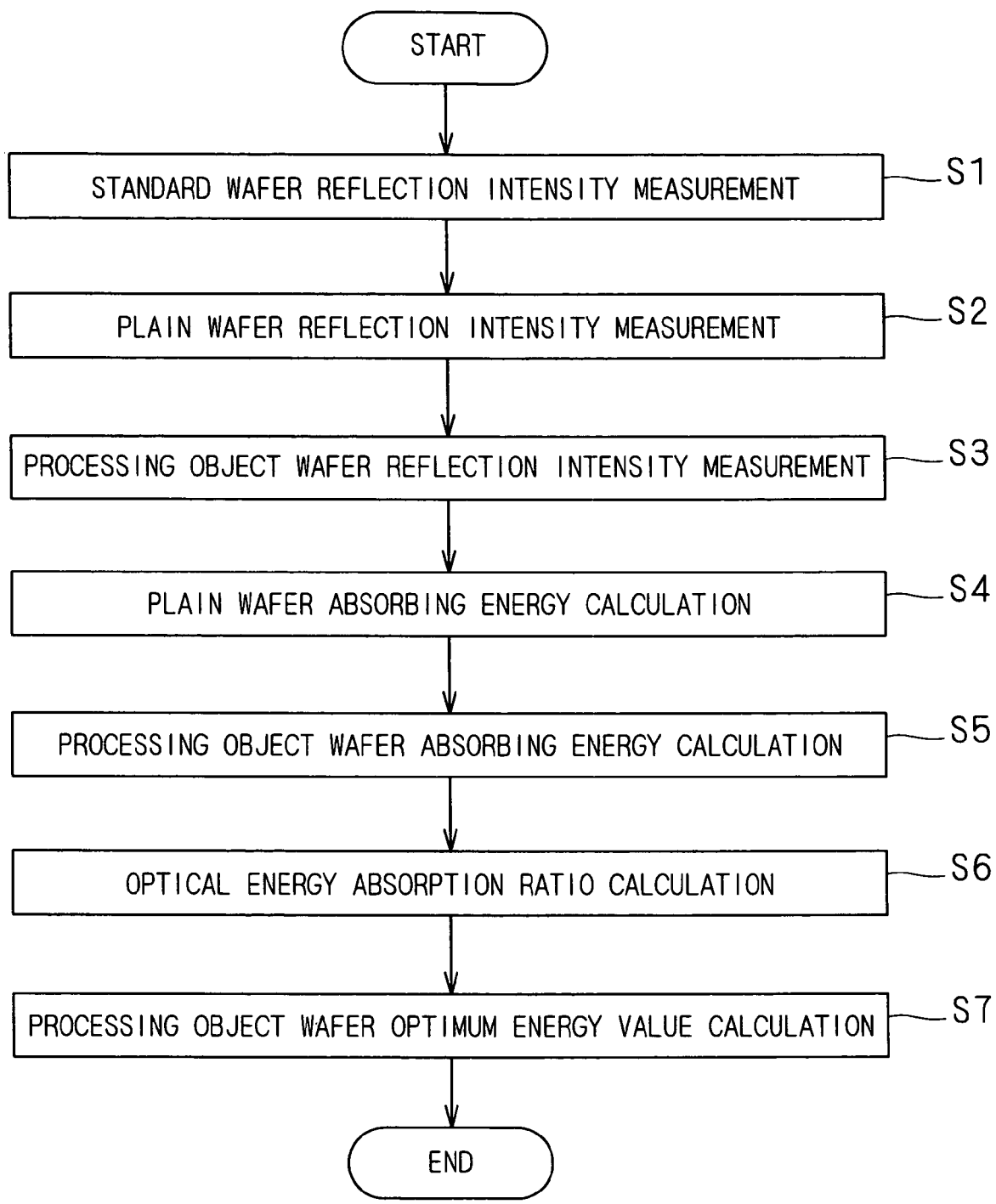
FIG. 8 is a flowchart showing a procedure in measuring optical energy absorption ratio of a semiconductor wafer in the alignment part.

FIG. 8 is a flowchart showing a procedure in measuring the optical energy absorption ratio of a semiconductor wafer W in the alignment part 130. Prior to that the semiconductor wafer W to be processed practically is processed along the above-mentioned wafer flow, a standard wafer of which reflectance is known, and a plain wafer on which no pattern is formed are transferred into the alignment part 130 to measure their respective reflection intensities.

First, the reflection intensity of the standard wafer with the known reflectance is measured (step S1). As a standard wafer, there may be employed one that is obtained by depositing Al on a glass pane. For such a standard wafer, the surface thereof is a mirror-finished surface, and therefore its reflectance is approximately 100%. This standard wafer is transferred into the alignment part 130 and mounted on the pins, and light is irradiated from the measuring optical system 31 to the surface of the standard wafer. The reflected light reflected from the surface of the standard wafer is then subjected to spectral resolution processing by the spectroscope 35. As the result of this processing, the spectral characteristics of the reflection intensity of the reflected light is inputted to the controller 10. In this specification, the spectral characteristics of the reflection intensity of the standard wafer is defined as standard reflection intensity.

Next, the reflection intensity of the plain wafer on which no pattern is formed is measured (step S2). The plain wafer is the same as the semiconductor wafer W to be treated normally, except for the point of being untreated substrate on which no pattern is formed. This plain wafer is transferred into the alignment part 130 and mounted on the pins, and light is irradiated from the measuring optical system 31 to the surface of the plain wafer. The reflected light reflected from the surface of the plain wafer is then subjected to spectral resolution processing by the spectroscope 35. As the result of this processing, the spectral characteristics of the reflection intensity of the reflected light is inputted to the controller 10. In this specification, the spectral characteristics of the reflection intensity of the plain wafer is defined as plain substrate reflection intensity.

The measurements of the standard reflection intensity and the plain substrate reflection intensity may be made once prior to the processing of a semiconductor wafer W to be processed normally. The standard reflection intensity and the plain substrate reflection intensity so obtained are then stored in the magnetic disk 14 of the controller 10.

Subsequently, the reflection intensity of a semiconductor wafer W to be processed practically is measured (step S3). This measurement is made every time that a processing object semiconductor wafer W is transferred for alignment into the alignment part 130. Since the semiconductor wafer to be processed practically is already subjected to ion implantation, a pattern is already formed thereon. From the measuring optical system 31, light is irradiated to the surface of the semiconductor wafer W transferred into the alignment part 130 and mounted on the pins by the transfer robot 120. The reflected light reflected from the surface of the processing object semiconductor wafer W is then subjected to spectral resolution processing by the spectroscope 35. As the result of this processing, the spectral characteristics of the reflection intensity of the reflected light is inputted to the controller 10. In this specification, the spectral characteristics of the reflection intensity of the processing object semiconductor wafer W is defined as processing object substrate reflection intensity. The reason why the reflection intensity measurement of the processing object semiconductor wafer W is made every time it is transferred into the alignment part 130 is that the reflection intensity of wafer could be different for different pattern formation contents.

Figure 9:
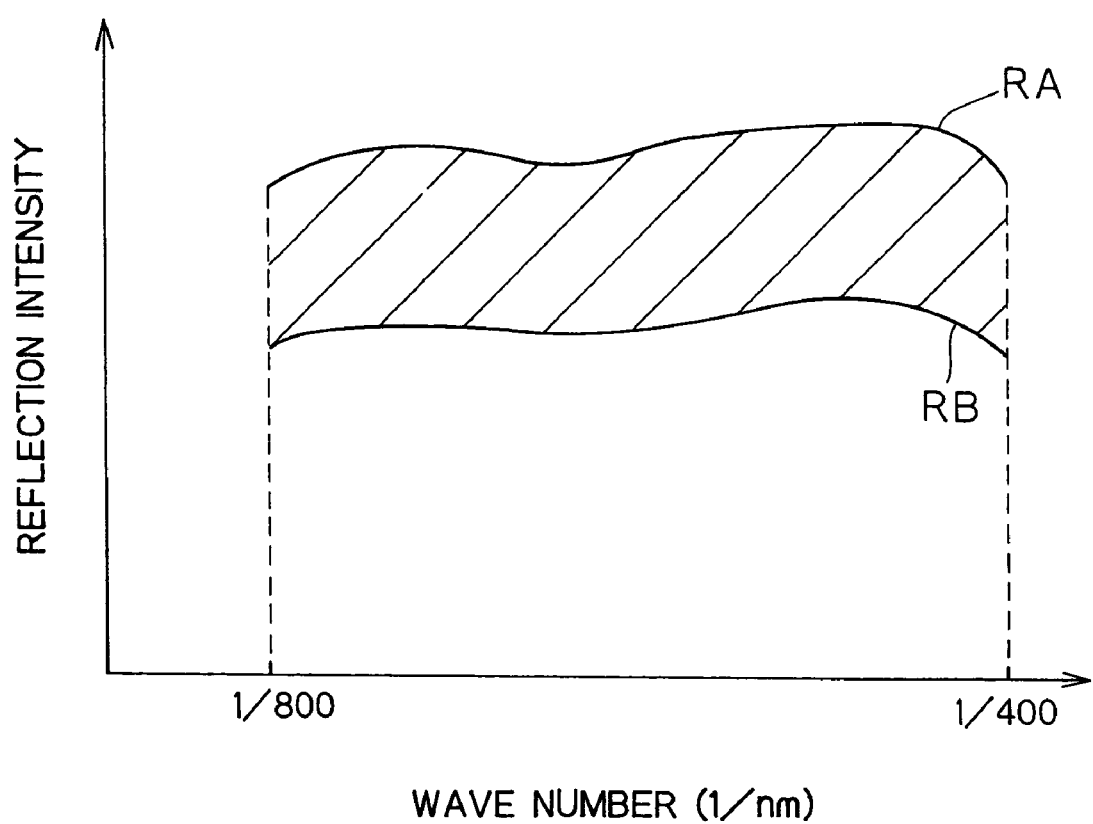
FIG. 9 is a diagram to explain optical energy absorbed by a plain wafer.

At the completion of the reflection intensity measurement of the processing object semiconductor wafer W, the flow advances to step S4 to calculate the optical energy absorbed by the plain wafer at the CPU 11 of the controller 10. FIG. 9 is a diagram to explain the optical energy absorbed by the plain wafer. In FIG. 9, the ordinate represents reflection intensity and the abscissa represents wave number (the inverse number of wavelength). The value of integration of reflection intensity on this two-dimensional coordinate gives the optical energy of reflected light. That is, in FIG. 9, the value obtained by the integration of standard reflection intensity RA gives optical energy SA of reflected light of the standard wafer, and the value obtained by the integration of plain substrate reflection intensity RB gives optical energy SB of reflected light of the plain wafer. Accordingly, assuming that the reflectance of the standard wafer is approximately 100%, the value obtained by subtracting the optical energy SB from the optical energy SA (i.e., the area indicated by slant lines in FIG. 9) is calculated as the optical energy absorbed by the plain wafer.

In the above description, the reason why the range of integration of reflection intensity is set to 1/800 to 1/400, namely visible light range, is that a wavelength range contributing to heating of the semiconductor wafer W is selected by taking into consideration that the wavelength distribution of the xenon flash lamps 69 extends from ultraviolet range to infrared range, and that the semiconductor wafer W of silicon transmits the infrared rays.

Figure 10:
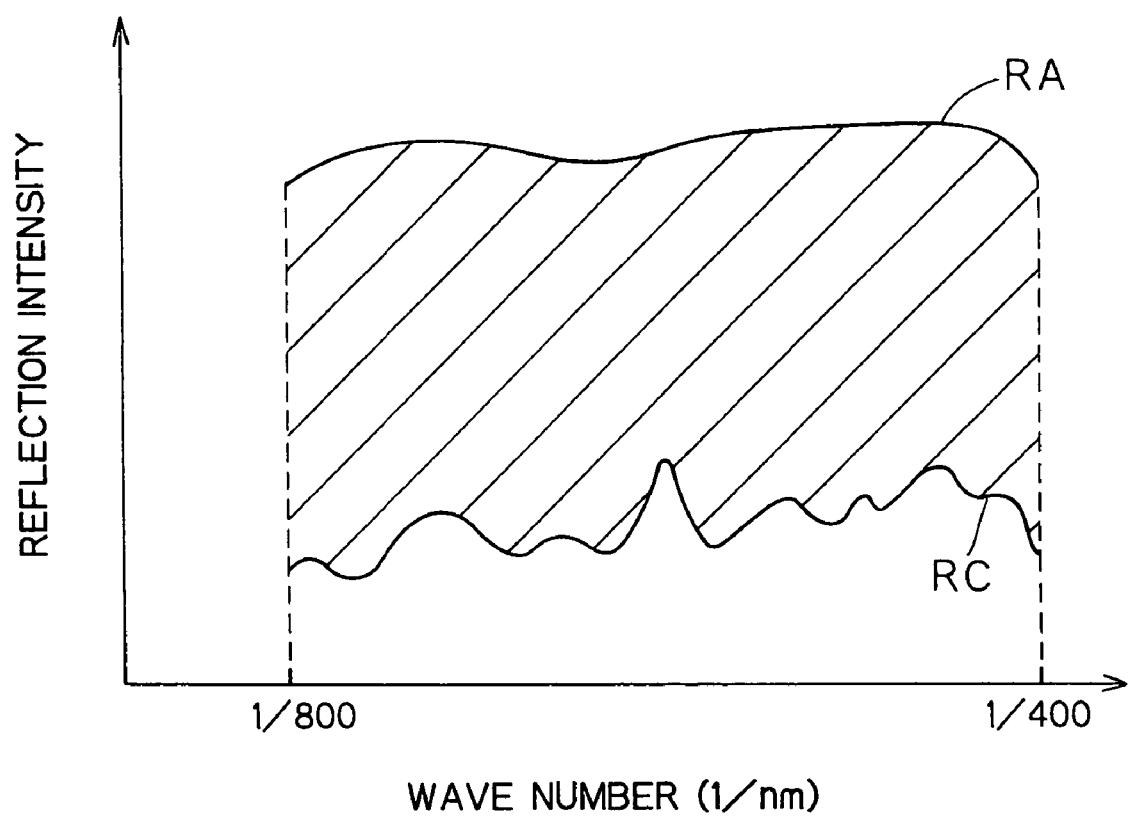
FIG. 10 is a diagram to explain optical energy absorbed by an object semiconductor wafer.

Then, the flow advances to step S5 to calculate the optical energy absorbed by the processing object semiconductor wafer W at the CPU 11 of the controller 10. FIG. 10 is a diagram to explain the optical energy absorbed by the processing object semiconductor wafer W. In FIG. 10, the value obtained by the integration of standard reflection intensity RA gives optical energy SA of reflected light of the standard wafer, and the value obtained by the integration of processing object substrate reflection intensity RC gives optical energy SC of reflected light of the processing object semiconductor wafer W. Accordingly, the value obtained by subtracting the optical energy SC from the optical energy SA (i.e., the area indicated by slant lines in FIG. 10) is calculated as the optical energy absorbed by the processing object semiconductor wafer W.

Thus, the optical energy absorbed by the plain wafer and the optical energy absorbed by the processing object semiconductor wafer W are calculated. From these, the CPU 11 of the controller 10 calculates the optical energy absorption ratio of the processing object semiconductor wafer W to the plain wafer (step S6). In other words, the optical energy absorption ratio r of the processing object semiconductor wafer W to the plain wafer is calculated from the following equation (1):

$$r = \frac{SA - SC}{SA - SB} \quad (1)$$

Because the processing object semiconductor wafer W usually absorbs more light than the plain wafer on which no pattern is formed, it follows normally SB>SC, resulting in r>1.

This enables to simply measure the optical energy absorption ratio r of the processing object semiconductor wafer W to the plain wafer by a simple optical system.

After the optical energy absorption ratio r of the processing object semiconductor wafer W to the plain wafer is calculated in the foregoing manner, an optimum value of optical energy irradiated from the flash lamps 69 to the processing object semiconductor wafer W is calculated in the first preferred embodiment (step S7). As described above, the energy value of flashlight irradiated from the flash lamps 69 is adjusted on the basis of the result of measurement that is made of the characteristic after processing (e.g., sheet resistance value etc.), which is obtained by performing ion implantation of a bare wafer on which no pattern is formed, and then practically performing flashlight irradiation to the ion-implanted plain wafer. In other words, the ion-implanted plain wafer has a known optimum energy value of light irradiated. As used herein, the term "the optimum energy value of light irradiated" indicates the necessary and sufficient energy value at which it is able to carry out ion activation without causing damage to the wafer. The optimum energy value of normal plain wafer is approximately 25 J/cm$^2$ to 28 J/cm$^2$.

However, for the above reason that the processing object semiconductor wafer W absorbs more light than the plain wafer, when flashlight of energy equivalent to that to the plain wafer, even if being an optimum value for the plain wafer, is irradiated to a practical processing object wafer, the surface temperature elevates than estimated, so that a wafer break might occur, as previously described.

Therefore, in the first preferred embodiment, based on the optimum energy value of light to be irradiated to the ion-implanted plain wafer and the above-mentioned optical energy absorption ratio r, the CPU 11 of the controller 10 calculates an optimum value of energy of flashlight irradiated to the processing object semiconductor wafer W, and the lamp power supply 99 is controlled to perform flashlight irradiation at the optimum value. Concretely, the CPU 11 of the controller 10 calculates an optimum value EC of energy of flashlight irradiated to the processing object semiconductor wafer W from the following equation (2):

$$EC = \frac{1}{r} \cdot EB \qquad (2)$$

where EB is an optimum energy value of light to be irradiated to the ion-implanted plain wafer.

This optimum energy value EB is the above-mentioned value previously found by experiments and simulation, etc. In other words, the optimum value EC of energy of light irradiated to the processing object semiconductor wafer W is calculated from the optimum energy value EB of light to be irradiated to the ion implanted plain wafer and the optical energy absorption ratio r. Hereat, because it is normally r>1, it follows that: EC<EB.

At the completion of the calculation of the optimum value EC of energy of light irradiated to the processing object semiconductor wafer W, the CPU 11 of the controller 10 controls the lamp power supply 99 such that flashlight irradiation of the optimum value EC is effected from the light source 5. Concretely, the voltage charged in a capacitor connected to the electrodes of the flash lamps 69 is adjusted according to the instruction from the controller 10. The voltage charged in the capacitor defines the amount of electric charge, by which the energy value of flashlight irradiated from the flash lamps 69 is defined.

There is a slight difference in reflectance between the ion-implanted plain wafer and a complete bare wafer not yet subjected to ion implantation, and the optimum energy value EB of light to be irradiated to the plain wafer, which is the basis for calculating the optimum value EC of energy of light to be irradiated to the processing object semiconductor wafer W, is the value obtained for the ion-implanted plain wafer. It is therefore preferable that the plain wafer used for calculating the optical energy absorption ratio r (the plain wafer of which reflection intensity is measured in the alignment part 130) is also an ion-implanted plain wafer.

The description of the processing operation in the processing part 160 is now continued. In the processing part 160, in the state that the susceptor 73 and the heating plate 74 are in the loading and unloading positions of a semiconductor wafer W as shown in FIG. 3, the semiconductor wafer W is loaded through the opening part 66 by the transport robot 150 and then mounted on the support pins 70. The optical energy absorption ratio r of this semiconductor wafer W is already measured in the alignment part 130, and the optimum value EC of energy of flashlight to be irradiated to this semiconductor wafer W is also already calculated. At the completion of the loading of the semiconductor wafer W, the gate valve 68 closes the opening part 66. Thereafter, the motor 40 drives the susceptor 73 and the heating plate 74 to move up to the thermal processing position of a semiconductor wafer W shown in FIG. 4, and then holds it in its horizontal position. Also, the switching valves 80 and 81 are opened to form a gas current of nitrogen gas in the chamber 65.

The susceptor 73 and the heating plate 74 are preheated to a predetermined temperature by the operation of the heater contained in the heating plate 74. Therefore, in the state in which the susceptor 73 and the heating plate 74 are in the thermal processing position of the semiconductor wafer W, the semiconductor wafer W is preheated by making contact with the susceptor 73 in its preheated state, so that the temperature of the semiconductor wafer W increases gradually.

In this state, the semiconductor wafer W is continuously heated by the susceptor 73. During the time that the temperature of the semiconductor wafer W is increasing, a temperature sensor (not shown) in the inside of the heating plate 74 always monitors whether the internal temperature of the heating plate 74 reaches a setting temperature at which the surface temperature of the semiconductor wafer W reaches a preheating temperature T1.

The preheating temperature T1 is, for example, about 200° C. to about 600° C. Even when the semiconductor wafer W is heated to the preheating temperature T1 in this temperature range, the ions implanted into the semiconductor wafer W do not diffuse.

Then, when the surface temperature of the semiconductor wafer W reaches the preheating temperature T1, the flash lamps 69 light up to perform flash heating. At this time, flashlight irradiation having the optimum value EC of energy of light to be irradiated to the semiconductor wafer W, which is previously calculated in the foregoing manner, is effected from flash lamps 69. The lighting time of the flash lamps 69 in this flash heating step is about 0.1 milliseconds to about 10 milliseconds. Thus, extremely intense flashes can be irradiated from the flash lamps 69 because the static energy previously stored is converted to such extremely short optical pulses.

The surface temperature of the semiconductor wafer W momentarily reaches temperature T2 by the above flash heating. The temperature T2 is about 1000° C. to about 1100° C., which is required for ion activation processing of the semiconductor wafer W. Elevating the temperature of the surface of the semiconductor wafer W to the processing temperature T2 can activate the ions implanted into the semiconductor wafer W.

At this time, the surface temperature of the semiconductor wafer W is elevated to the processing temperature T2 in an extremely short time of about 0.1 milliseconds to about 10 milliseconds, thereby completing the activation of the ions in the semiconductor wafer W in a short period of time. Therefore, the ions implanted into the semiconductor wafer W do not diffuse, thereby avoiding the phenomenon that the profile of the ions implanted into the semiconductor wafer W becomes round. Note that since the time required for ion implantation is extremely shorter than the time required for ion diffusion, the ion activation is completed even in such a short period of time, about 0.1 milliseconds to about 10 milliseconds, which is too short to cause diffusion.

Additionally, since the flashlight irradiation having the optimum value EC of energy of light to be irradiated to the processing object semiconductor wafer W is effected from the flash lamps 69, the ion activation can be carried out without causing damage to the semiconductor wafer W during thermal processing.

Before the flash lamps 69 light up to heat the semiconductor wafer W, the surface temperature of the semiconductor wafer W is already heated to the preheating temperature T1 of about 200° C. to about 600° C., by use of the heating plate 74. It is therefore possible to quickly elevate the semiconductor wafer W to the processing temperature T2 of about 1000° C. to about 1100° C., by use of the flash lamps 69.

After the flash heating step is terminated, the motor 40 drives the susceptor 73 and the heating plate 74 to move down to the loading and unloading positions of the semiconductor wafer W shown in FIG. 3. At the same time, the opening part 66 that has been closed by the gate valve 68 is opened. The transport robot 150 then unloads the semiconductor wafer W mounted on the support pins 70. Thus, a sequence of the thermal processing operation is completed.

2. Second Preferred Embodiment

The following is a second preferred embodiment of the present invention. The arrangement of a thermal processing apparatus and thermal processing operation to a semiconductor wafer W in the second preferred embodiment are the same as in the first preferred embodiment, and the description thereof is omitted. The second preferred embodiment differs from the first preferred embodiment in the use of an optical energy absorption ratio r of a processing object semiconductor wafer W to a plain wafer. Specifically, in the second preferred embodiment, an estimated temperature of the processing object semiconductor wafer W during flash heating is calculated from the optical energy absorption ratio r.

FIG. 11 is a flowchart showing a procedure in calculating an estimated temperature of a processing object semiconductor wafer W during flash heating. In FIG. 11, the processing procedure of steps S1 to S16 is completely the same as the processing procedure of steps S1 to S6 in FIG. 8. That is, the optical energy absorption ratio r of the processing object semiconductor wafer W to the plain wafer on which no pattern is formed is calculated in the same manner as in the first preferred embodiment.

Then, in the second preferred embodiment, the estimated temperature of arrival of the semiconductor wafer W during flash heating is calculated on the basis of the calculated optical energy absorption ratio r (step S17). As described above, the energy value of light irradiated from the flash lamps 69 is adjusted on the basis of the result of measurement, the characteristic after processing, which is obtained by performing ion implantation of a bare wafer on which no pattern is formed, and then practically performing flashlight irradiation to the ion-implanted plain wafer. That is, in the normal state, the energy value of flashlight irradiated from the flash lamps 69 is set to an optimum energy value of flashlight to be irradiated to the ion-implanted plain wafer.

However, because the processing object semiconductor wafer W absorbs more light than the plain wafer, when flashlight of an optimum energy value for the plain wafer is irradiated to a wafer to be processed practically, its surface temperature elevates than estimated. In the second preferred embodiment, the CPU 11 of the controller 10 calculates an estimated temperature when light of optimum energy value for the plain wafer is irradiated to the semiconductor wafer W to be processed practically.

Concretely, first, the correlation between the energy value of light irradiated to an ion-implanted plain wafer on which no pattern is formed and the temperature of this plain wafer is previously found by experiments and simulation, etc. The CPU 11 calculates r·EB, which is obtained by multiplying an optimum energy value EB of light to be irradiated to the plain wafer by an optical energy absorption ratio r. This r·EB is an energy value of irradiation light required to have the plain wafer absorb energy equal to the energy that a processing object semiconductor wafer W absorbs when irradiating light of the energy value EB to this semiconductor wafer W. Accordingly, in the correlation between the energy value of light irradiated to a plain wafer and the temperature of the plain wafer, the temperature corresponding to r·EB is an estimated temperature at which the processing object semiconductor wafer W arrives when the light of the energy value EB is irradiated to this semiconductor wafer W.

Thus, in the second preferred embodiment, the estimated temperature of the processing object semiconductor wafer W during flash heating is readily calculated on the basis of the correlation between the energy value of light irradiated to the ion-implanted plain wafer on which no pattern is formed and the temperature of this plain wafer, and the optical energy absorption ratio r of the processing object semiconductor wafer W to the plain wafer.

Then, the CPU 11 compares the estimated temperature so calculated and a predetermined threshold value (step S18). The predetermined threshold value. may be preset as a temperature at which a semiconductor wafer W causes slip, for example. As a result of the comparison, when the obtained estimated temperature of the processing object semiconductor wafer W during flash heating exceeds the threshold value, the flow advances to step S19 to provide a warning by the controller 10. The warning may be provided, for example, by displaying a warning message on a display part 21.

On the other hand, when the estimated temperature is not more than the threshold value, the processing may be continued to perform flash heating by the flash lamps 69.

In accordance with the second preferred embodiment, prior to flash heating, it is possible to calculate the estimated temperature of arrival of the processing object semiconductor wafer W. Therefore, by adjusting, based on it, the energy value of light irradiated from the flash lamps 69, it is able to prevent damage to the semiconductor wafer W during thermal processing.

Since in the second preferred embodiment, the estimated temperature of a processing object semiconductor wafer W during flash heating is readily calculated on the basis of the correlation between the energy value of light irradiated to an ion-implanted plain wafer on which no pattern is formed and the temperature of this plain wafer, and the optical energy absorption ratio r of the processing object semiconductor wafer W to the plain wafer, it is preferable that the plain wafer used for calculating the optical energy absorption ratio r (the plain wafer of which reflection intensity is measured in the alignment part 130) is also an ion-implanted plain wafer. In the case where the correlation between an energy value of light irradiated to a plain wafer subjected to neither pattern formation nor ion implantation (i.e., a complete bare wafer) and the temperature of this bare wafer is previously found by experiments and simulation, etc., it is suitable to calculate the estimated temperature of a processing object semiconductor wafer W during flash heating on the basis of this correlation and the optical energy absorption ratio r of this semiconductor wafer W to this bare wafer. It is therefore preferable that the plain wafer used for calculating an optical energy absorption ratio r is also a complete bare wafer not yet subjected to ion implantation.

3. Third Preferred Embodiment

The following is a third preferred embodiment of the present invention. The arrangement of a thermal processing apparatus and thermal processing operation to a semiconductor wafer W in the third preferred embodiment are the same as in the first preferred embodiment, and the description thereof is omitted. The third preferred embodiment differs from the first preferred embodiment in the method of calculating an optical energy absorption ratio r of a processing object semiconductor wafer W to a plain wafer. In the third preferred embodiment, the optical absorption ratio r is calculated without using a standard wafer.

FIG. 12 is a flowchart showing other example of measuring procedure of an optical energy absorption ratio of a semiconductor wafer W. Prior to execution of this measuring procedure, the reflectance of an ion-implanted plain wafer on which no pattern is previously found by experiments. This reflectance is stored in a RAM 13 and a magnetic disk 14. Thus, under the condition that the reflectance of the plain wafer is known, the reflection intensity of the plain wafer is measured (step S21). If the plain wafer with a known reflectance is already subjected to ion implantation, the reflection intensity measurement is also made of the ion-implanted one. This measurement itself is the same as in step S2 of the first preferred embodiment, and the reflection intensity of the plain substrate is obtained by this measurement.

Then, based on the plain substrate reflection intensity and the known reflectance of the plain wafer, the CPU 11 calculates an ideal reflection intensity, which is the spectral reflection intensity of reflected light obtained when irradiating light to an ideal mirror of which reflectance is 100% (step S22). Concretely, the ideal reflection intensity is calculated by dividing the plain substrate reflection intensity obtained in step S21, by the reflectance of the plain wafer. This ideal reflection intensity is substantially equal to the spectral reflection intensity of the standard wafer (the standard reflection intensity), the reflectance of which is approximately 100% in the first preferred embodiment.

The contents of the processing procedure of steps S23 to S27 in FIG. 12 are completely the same as that in steps S3 to S7 in FIG. 8. However, in the third preferred embodiment, the ideal reflection intensity is used instead of the standard reflection intensity. Specifically, after making the reflection intensity measurement of the semiconductor wafer W to be processed practically (step S23), instead of the standard reflection intensity RA, the ideal reflection intensity is used to calculate the optical energy absorbed by the plain wafer and the optical energy absorbed by the processing object semiconductor wafer W (step S24, step S25). From these, the CPU 11 of the controller 10 calculates the optical energy absorption ratio of the processing object semiconductor wafer W to the plain wafer (step S26). Thereafter, in the same manner as in the first preferred embodiment, based on the optimum energy value of light irradiated to the ion-implanted plain wafer and the above optical energy absorption ratio, the optimum value of energy of flashlight irradiated to the processing object semiconductor wafer W is calculated (step S27).

Thus, in the third preferred embodiment, instead of measuring the spectral reflection intensity of the standard wafer of which reflectance is approximately 100%, the spectral reflection intensity of the plain wafer with a known reflectance is measured, and from the measuring result, there is calculated the ideal reflection intensity to be obtained when irradiating light to the ideal mirror having a reflectance of 100%. Then, instead of the standard reflection intensity, the ideal reflection intensity is used to calculate the optical energy absorption ratio r. Even in this manner, the physical significance of the ideal reflection intensity is the same as the standard reflection intensity. Hence, like the first preferred embodiment, it is able to calculate the optimum value EC of energy of light irradiated to the processing object semiconductor wafer W. The third preferred does not employ any standard wafer obtained by depositing A1 on a glass pane, which is relatively expensive, thus permitting to suppress cost increase.

In the third preferred embodiment, the ideal reflection intensity is calculated by measuring the reflection intensity of the ion-implanted plain wafer. Alternatively, the ideal reflection intensity may be calculated by measuring the reflection intensity of a plain wafer subjected to neither pattern formation nor ion implantation (i.e., a complete bare wafer). The reflectance of the completely bare wafer is widely known. Therefore, the ideal reflection intensity may be calculated from the plain substrate reflection intensity obtained by the reflection intensity measurement of the bare wafer. This enables to easily calculate the accurate ideal reflection intensity. Even with this case, however, the optimum energy value of light to be irradiated to the plain wafer, which is the basis for calculating the optimum value of energy of light irradiated to the processing object semiconductor wafer W, is the value obtained for the ion-implanted plain wafer. It is therefore preferable that the plain substrate reflection intensity used for calculating the optical energy absorbed by the plain wafer is found by actual measurement of the ion-implanted plain wafer. In addition, the determination of the plain substrate reflection intensity may be made once prior to the processing of the semiconductor wafer W to be processed normally.

4. Fourth Preferred Embodiment

The following is a fourth preferred embodiment of the present invention. The arrangement of a thermal processing apparatus and thermal processing operation to a semiconductor wafer W in the processing part 160 are the same as in the first preferred embodiment. In the fourth preferred embodiment, the estimated temperature of arrival of a processing object semiconductor wafer W during flash heating is calculated in real time.

Figure 13:
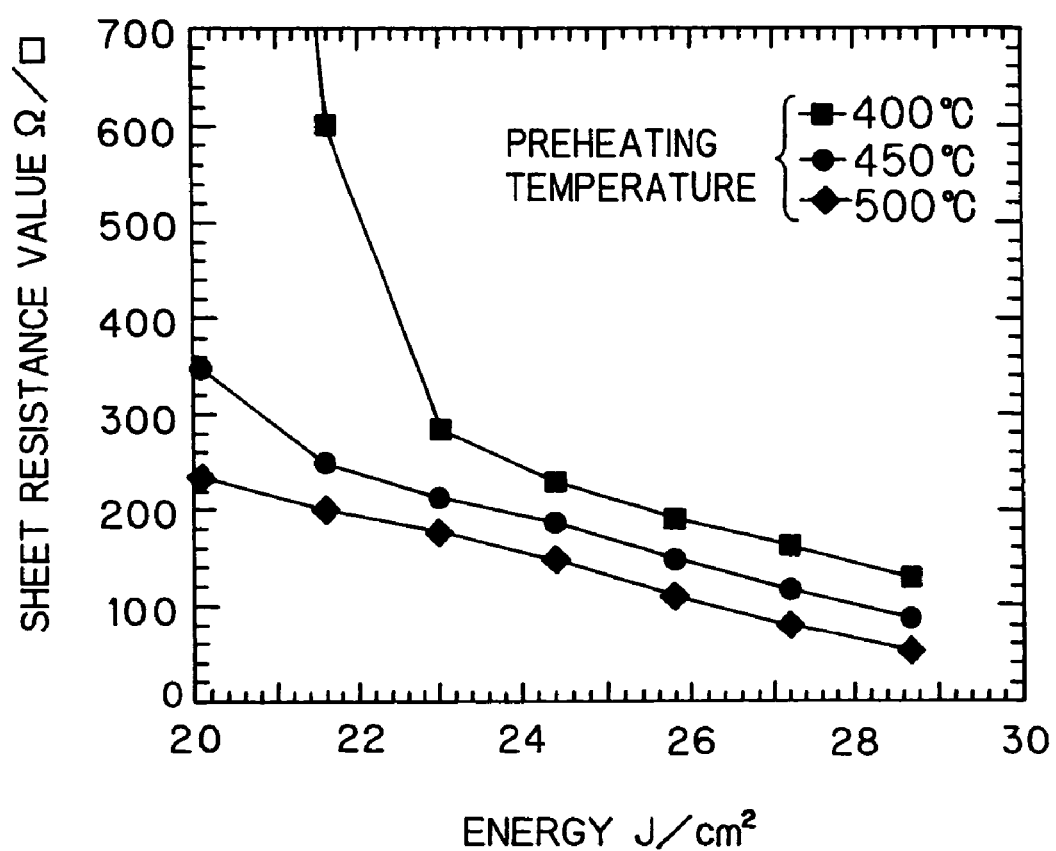
FIG. 13 is a diagram showing the correlation between irradiation energy and sheet resistance value when an ion-implanted plain wafer is subjected to flash heating.

FIG. 13 is a diagram showing the correlation between irradiation energy and sheet resistance value when performing flash heating of an ion-implanted plain wafer. The sheet resistance value is an index indicating a surface temperature at which the wafer arrives, and a measured value obtained by applying four-terminal method to the plain wafer after flash heating. The same sheet resistance indicates the same surface temperature at which the wafer arrives during flash heating. In this measurement, at three preheating temperatures of 400° C., 450° C., and 500° C., sheet resistance value is measured by changing irradiation light energy for each preheating temperature.

As shown in FIG. 13, irrespective of preheating temperature, a good linear relationship can be confirmed in the correlation between irradiation light energy and sheet resistance in the range of 23 J/cm$^2$ to 29 J/cm$^2$ in irradiation light energy. In addition, irrespective of preheating temperature, the gradient in a linear region is substantially constant. From this, it can be considered that the preheating temperature of 50° C. corresponds to about 2 J/cm$^2$ in irradiation energy. In other words, even if reducing the preheating temperature 50° C., the wafer surface temperature can be approximately the same by increasing irradiation energy about 2 J/cm$^2$. It is assumed that the irradiation light energy of 1 J/cm$^2$ elevates the wafer surface temperature about 25° C. Accordingly, the surface temperature of arrival during the flash heating of an ion-implanted plain wafer can be expressed by the following equation (3):

$$Ts = Ta + 25J \tag{3}$$

where Ts is a surface temperature of arrival during flash heating of the ion-implanted plain wafer, Ta is a preheating temperature, and J is an irradiation light energy during flash heating.

As previously described in the second preferred embodiment, when flashlight of energy J is irradiated to the semiconductor wafer W to be processed practically, energy of r·J, which is obtained by multiplying the energy J by the optical energy absorption ratio r of the processing object semiconductor wafer W to the plain wafer. Accordingly, the surface temperature of arrival, Tserf, when flashlight of irradiation light energy is irradiated to the processing object semiconductor wafer can be expressed by the following equation (4):

$$Tserf=Ta+25rJ \quad (4)$$

Since it is impossible to directly observe the irradiation light energy J during flash heating, radiation light intensity M from the flash lamps 69 is used, which is measured on a power monitor 83. By the investigation of the present inventor, it has been found that there is a correlation of linear relationship between the radiation light intensity M from the flash lamps 69 that is observed on the power monitor 83, and the irradiation light energy J. Letting its coefficient be β, finally, the surface temperature of arrival Tserf of the processing object semiconductor wafer W during flash heating can be expressed by the following equation (5):

$$Tserf=Ta+25r\beta M \quad (5)$$

When performing flash heating of the processing object semiconductor wafer W, the CPU 11 of the controller 10 calculates the surface temperature of arrival of the semiconductor wafer W by the equation (5), from a preheating temperature Ta, an optical energy absorption ratio r, and a coefficient β, which are previously found, and a radiation light intensity M, which is practically measured on the power monitor 83. The calculated surface temperature of arrival Tserf may be displayed on, for example, the display part 21.

5. Modifications

While the preferred embodiments of the present invention have been described, these preferred embodiments are illustrative and should not be viewed as limiting the present invention. For example, although in the foregoing preferred embodiments, the light source 5 is provided with the thirty flash lamps 69, without limiting to this, the number of flash lamps 69 may be determined at will.

Alternatively, instead of the flash lamps 69, the light source 5 may be provided with lamps of other type (e.g., halogen lamps), so that heating of a semiconductor wafer W is effected by light irradiation from these lamps. The technique of the present invention is applicable to such a thermal processing apparatus. Even in this case, it is possible to calculate the optimum value of energy of light irradiated to a processing object semiconductor wafer W from the optical energy absorption ratio of this semiconductor wafer W to a bare wafer, and to calculate the estimated temperature of arrival of the semiconductor wafer W during thermal processing.

Although in the foregoing preferred embodiments, the two carriers 91 are mounted in the substrate storing part 110, the number of the carrier 91 may be only one, or not less than three. Although the transfer robot 120 is constructed to move between the two carriers 91, two transfer robots 120 may be provided.

In an alternative, the upper transport arm 151a of the transport robot 150 may be designed as an arm exclusively for holding an untreated semiconductor wafer W, and the lower transport arm 151b may be designed as an arm exclusively for holding a treated semiconductor wafer W. Thereby it is capable of miniaturizing the transport robot 150 and improving the reliability of transport.

As a standard wafer, it should not be limited to one that is obtained by depositing Al on a glass pane, and any wafer of which reflectance is known may be used. This is because if the reflectance is known, the reflection intensity at the time of total reflection can be determined from the reflectance and reflection intensity.

Although the absorption ratio measuring apparatus 30 is disposed in the alignment part 130, without limiting to this, it may be disposed at any location on the path on which a semiconductor wafer W is transported from the substrate storing part 110 to the processing part 160.

In the second preferred embodiment, the arrangement is such that light having an optimum energy value for plain wafer is irradiated to a semiconductor wafer W to be processed practically. Without limiting to this, in the case where light having a known energy value is irradiated to a semiconductor wafer W to be processed practically, the estimated temperature of arrival of this semiconductor wafer W during thermal processing can be calculated from the known energy value and the optical energy absorption ratio r of the semiconductor wafer W to a plain wafer.

Although in the foregoing preferred embodiments, the ion activation process is effected by irradiating light to a semiconductor wafer, a substrate to be processed by the thermal processing apparatus of the present invention is not limited to a semiconductor wafer. For example, the thermal processing apparatus of the present invention may be used to process a glass substrate in which a variety of silicon films such as a silicon nitride film and a polycrystal silicon film are formed. As an example, to a polycrystal silicon film that is formed on a glass substrate by CVD method, ion implantation of silicon is performed to form an amorphous silicon film that is made into amorphous, and a silicon oxide film serving as an antireflection film is formed on the amorphous silicon film. In this state, the thermal processing apparatus of the present invention may perform light irradiation to the entire surface of the amorphous silicon film, thereby forming a polycrystal silicon film that is derived from polycrystallization of the amorphous silicon film.

In an alternative, to a TFT substrate, which is obtained by the step of forming on a glass substrate an underlayer oxide silicon film and a polysilicon film derived from the crystallization of amorphous silicon, and the step of doping impurities such as phosphor or boron into the polysilicon film, the thermal processing apparatus of the present invention may perform light irradiation to activate the impurities implanted in the doping step.

While the invention has been shown and described in detail, the foregoing description is in all aspects illustrative and not restrictive. It is therefore understood that numerous modifications and variations can be devised without departing from the scope of the invention.

What is claimed is:

1. A thermal processing apparatus for heating a processing object substrate by irradiating light to said substrate, with a known optimum energy value of light irradiated to a plain substrate on which no pattern is formed, said apparatus comprising:

a) a holding element for holding said processing object substrate;

b) an irradiation element with a lamp for irradiating light to said processing object substrate held by said holding element;

c) a measuring apparatus comprising:

c-1) a plain substrate reflection intensity obtaining element for obtaining a plain substrate reflection intensity by measuring spectral characteristics of reflection intensity of a reflected light obtained when irradiating light to a plain substrate with a known reflectance;

c-2) an ideal reflection intensity calculating element for calculating an ideal reflection intensity that is a spectral reflection intensity of a reflected light when irradiating light to an ideal mirror of which reflectance is 10000, on the basis of said plain substrate reflection intensity and said reflectance;

c-3) a processing object substrate reflection intensity obtaining element for obtaining a processing object substrate reflection intensity by measuring spectral characteristics of reflection intensity of a reflected light obtained when irradiating light to said processing object substrate;

c-4) a plain substrate absorbing energy calculating element for calculating optical energy absorbed by said plain substrate from said ideal reflection intensity and said plain substrate reflection intensity;

c-5) a processing object substrate absorbing energy calculating element for calculating optical energy absorbed by said processing object substrate from said ideal reflection intensity and said processing object substrate reflection intensity; and c-6) an absorption ratio calculating element for calculating an optical energy absorption ratio of said optical energy absorbed by said processing object substrate to said optical energy absorbed by said plain substrate and said optical energy absorbed by said processing object substrate; and d) an optical energy control element for adjusting the energy of light irradiated from said irradiation element to said processing object substrate, on the basis of said optical energy absorption ratio obtained by said measuring apparatus and said optimum energy value of light irradiated to said plain substrate.

2. A thermal processing apparatus for heating a processing object substrate by irradiating flashlight to said substrate, with a known optimum energy value of flashlight irradiated to a plain substrate on which no pattern is formed, comprising:

a holding element for holding said processing object substrate;

an irradiation element with a flash lamp for irradiating a flashlight to said processing object substrate held by said holding element; and an optical energy control element for adjusting the energy of flashlight irradiated from said irradiation element to said processing object substrate, on the basis of an optical energy absorption ratio of said optical energy absorbed by said processing object substrate to said optimum energy value of flashlight irradiated to said plain substrate.

* * * * *